(12) United States Patent
Sim et al.

(10) Patent No.: US 9,616,115 B2
(45) Date of Patent: Apr. 11, 2017

(54) PURIFIED PLASMODIUM AND VACCINE COMPOSITIONS

(71) Applicant: Sanaria Inc., Rockville, MD (US)

(72) Inventors: B. Kim Lee Sim, Gaithersburg, MD (US); Minglin Li, Ellicott City, MD (US); Richard E. Stafford, Annandale, VA (US); Stephen L. Hoffman, Gaithersburg, MD (US)

(73) Assignee: SANARIA INC., Rockville, MD (US)

( * ) Notice: Subject to any disclaimer, the term of this patent is extended or adjusted under 35 U.S.C. 154(b) by 0 days.

(21) Appl. No.: 15/002,443

(22) Filed: Jan. 21, 2016

(65) Prior Publication Data

US 2016/0175417 A1 Jun. 23, 2016

Related U.S. Application Data

(60) Continuation of application No. 14/671,003, filed on Mar. 27, 2015, now Pat. No. 9,241,982, which is a continuation of application No. 13/730,281, filed on Dec. 28, 2012, now Pat. No. 8,992,944, which is a division of application No. 12/870,102, filed on Aug. 27, 2010, now Pat. No. 8,367,810, which is a division of application No. 12/684,863, filed on Jan. 8, 2010, now Pat. No. 8,043,625.

(60) Provisional application No. 61/202,001, filed on Jan. 16, 2009.

(51) Int. Cl.
| | |
|---|---|
| *A61K 39/002* | (2006.01) |
| *A61K 39/015* | (2006.01) |
| *A61K 9/00* | (2006.01) |
| *A61K 31/4706* | (2006.01) |
| *A61K 39/00* | (2006.01) |

(52) U.S. Cl.
CPC .......... *A61K 39/015* (2013.01); *A61K 9/0019* (2013.01); *A61K 31/4706* (2013.01); *A61K 2039/522* (2013.01); *A61K 2039/6081* (2013.01)

(58) Field of Classification Search
None
See application file for complete search history.

(56) References Cited

U.S. PATENT DOCUMENTS

| | | | |
|---|---|---|---|
| 4,850,305 A | 7/1989 | Georgi et al. | |
| RE35,348 E | 10/1996 | Georgi | |
| 5,766,597 A | 6/1998 | Paoletti et al. | |
| 5,983,557 A | 11/1999 | Perich et al. | |
| 7,122,179 B2 | 10/2006 | Kappe et al. | |
| 7,229,627 B2 | 6/2007 | Hoffman et al. | |
| 7,550,138 B1 | 6/2009 | Waters et al. | |
| 8,043,625 B2 | 10/2011 | Sim et al. | |
| 8,268,959 B2 | 9/2012 | Golding et al. | |
| 8,367,810 B2 | 2/2013 | Sim et al. | |
| 8,821,896 B2 | 9/2014 | Sim et al. | |
| 8,992,944 B2 | 3/2015 | Sim et al. | |
| 9,241,982 B2 | 1/2016 | Sim et al. | |
| 2005/0208078 A1 | 9/2005 | Hoffman et al. | |
| 2005/0220822 A1 | 10/2005 | Hoffman et al. | |
| 2005/0233435 A1 | 10/2005 | Kappe et al. | |
| 2007/0169209 A1 | 7/2007 | Hoffman et al. | |
| 2012/0156245 A1 | 6/2012 | Hoffman et al. | |
| 2012/0288525 A1 | 11/2012 | Chakravarty et al. | |
| 2012/0328645 A1 | 12/2012 | Hoffman et al. | |
| 2013/0224250 A1 | 8/2013 | Sim et al. | |
| 2015/0313980 A1 | 11/2015 | Janse et al. | |
| 2015/0313981 A1 | 11/2015 | Sim et al. | |

FOREIGN PATENT DOCUMENTS

| | | |
|---|---|---|
| CN | 1142887 A | 12/1995 |
| CN | 1213497 A | 10/1997 |
| GB | 1594721 A | 5/1978 |
| JP | 57156421 | 9/1982 |
| JP | 7-289119 | 7/1995 |
| WO | WO 91/16814 A1 | 11/1991 |
| WO | WO 92/11760 A1 | 7/1992 |
| WO | WO 95/26633 A2 | 7/1992 |
| WO | WO 00/74478 A1 | 12/2000 |
| WO | WO 03/087322 A2 | 10/2003 |
| WO | WO 2014/116990 A1 | 7/2014 |

OTHER PUBLICATIONS

Alonso, P.L., et al., "Efficacy of the RTS,S AS02A vaccine against *Plasmodium falciparum* infection and disease in young African children: randomized controlled trial," *Lancet* 364:1411-1420 (2004).
Beier, J.C., "Malaria Parasite Development in Mosquitoes," *Annu. Rev. Entomol.* 43:519-43 (1998).
Belnoue, E., et al., "Protective T Cell Immunity Against Malaria Liver Stage After Vaccination with Live Sporozoites Under Chloroquine Treatment," *The Journal of Immunology* 172:2487-2495, The American Association of Immunologists, United States (2004).
Breman, J.G., et al., "Defining and defeating the intolerable burden of malaria III. Progress and perspectives," *Am. J. Trop. Med. Hyg.* 77(*Suppl* 6):vi-xi, The American Society of Tropical Medicine and Hygiene, United States (2007).
Chattopadhyay et al., "The Effects of radiation on the safety and protective.efficacy of an attenuated *Plasmodium yoelii* sporozoite malaria vaccine," *Vaccine* 27:3675-3680 (2009).
Clyde, D.F., "Immunity to falciparum and vivax malaria induced by irradiated sporozoites: a review of the University of Maryland studies, 1971-75," *Bulletin of the World Health Organization* 68 (*Suppl.*):9-12, World Health Organization, Switzerland (1990).

(Continued)

*Primary Examiner* — Jennifer Graser
(74) *Attorney, Agent, or Firm* — Sterne, Kessler, Goldstein & Fox P.L.L.C.

(57) ABSTRACT

Disclosed are substantially purified *Plasmodium* sporozoites and preparations of *Plasmodium* sporozoites substantially separated from attendant non-sporozoite material, where the preparations of *Plasmodium* sporozoites have increasing levels of purity. Vaccines and pharmaceutical compositions comprising purified *Plasmodium* sporozoites are likewise provided. Methods of purifying preparations of *Plasmodium* sporozoites are also provided.

14 Claims, 3 Drawing Sheets

(56) References Cited

OTHER PUBLICATIONS

Figure 1A:
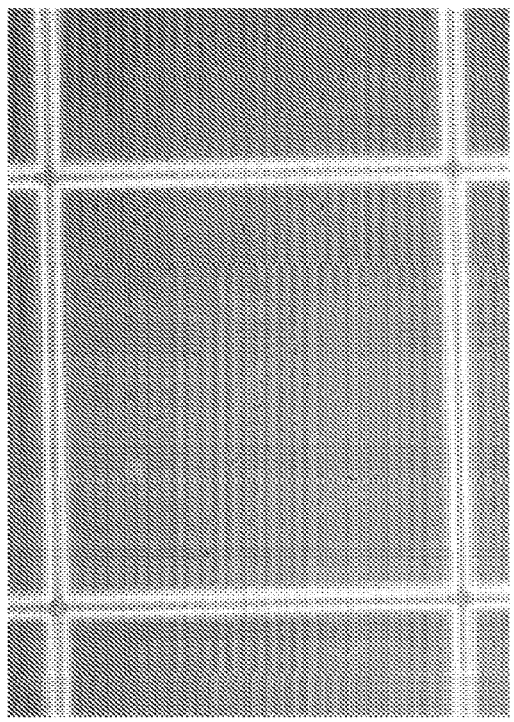

Daubenberger, C.A., "First clinical trial of purified, irradiated malaria sporozoites in humans," *Expert Rev. Vaccines* 11(1):31-33, Expert Reviews Ltd, England (2012).
Doolan, D.L. and Hoffman, S.L., "The Complexity of Protective Immunity Against Liver-Stage Malaria," *The Journal of Immunology* 165:1453-1462, The American Association of Immunologists, United States (2000).
Edelman, R., et al., "Long-Term Persistence of Sterile Immunity in a Volunteer Immunized with X-Irradiated Plasmodium falciparum Sporozoites," *The Journal of Infectious Diseases* 168:1066-1070, Infectious Diseases Society of America, United States (1993).
Editorial. "Malaria, 2010: more ambition and accountability please," *The Lancet* 375:1407, Lancet Publishing Group, England (2010).
Engelmann, S., et al., "Transgenic *Plasmodium berghei* sporozoites Expressing β-galactosidase for Quantification of Sporozoite Transmission," *Mol. Biochem. Parasitol.* 146(1): 30-37, Elsevier, Netherlands (2006).
Epstein, J.E. et al., "Malaria vaccines: are we getting closer?" *Curr. Opin. Mol. Ther.* 9(1):12-24 (2007).
Herrington, D.A., "Safety and immunogenicity in man of a synthetic peptide malaria vaccine against *Plasmodium falciparum* sporozoites," *Nature* 328:257-259, Nature Publishing Group, England (1987).
Herrington, D., et al., "Successful Immunization of Human with Irradiated Malaria Sporozoites: Humoral and Cellular Responses of the Protected Individuals," *Am. J. Trop. Med. Hyg.* 45(5):539-547, The American Society of Tropical Medicine and Hygiene, United States (1991).
Hoffman, S.L., et al., "Sporozoite Vaccine Induces Genetically Restricted T Cell Elimination of Malaria from Hepatocytes," *Science* 244:1078-1081, American Association for the Advancement of Science, United States (1989).
Hoffman, S.L., et al., "Protection of Humans against Malaria by Immunization with Radiation-Attenuated *Plasmodium falciparum* Sporozoites," *The Journal of Infectious Diseases* 185:1155-1164, the Infectious Diseases Society of America, United States (2002).
Hoffman, S.L., et al., "Development of a metabolically active, non-replicating sporozoite vaccine to prevent *Plasmodium falciparum* malaria," *Human Vaccines* 6:97-106, Landes Bioscience, United States (Jan. 2010).
Jiang, J-B., et al., "Induction of retarded exoerythrocytic schizonts by chloroguanide resulting in delayed parasitaemia of *Plasmodium inui* in *Macaca mulatta*," *Acta Pharmacologica. Sinica* 11(3):272-274, Shanghai Institute of Materia Medica (1990).
Kramer, L.D. and Vanderberg, J.P., "Intramuscular Immunization of Mice with Irradiated *Plasmodium berghei* Sporozoites," *The American Journal of Tropical Medicine and Hygiene* 24(6):913-916, The American Society of Tropical Medicine and Hygiene, United States (1975).
Krzych, U., et al., "T Lymphocytes from Volunteers Immunized with Irradiated *Plasmodium falciparum* Sporozoites Recognize Liver and Blood Stage Malaria Antigens," *J. Immunol.* 155:4072-4077, American Association of Immunologists, United States (1995).
Labaied et al., "*Plasmodium yoelii* Sporozoites with Simultaneous Deletion of P52 and P36 Are Completely Attenuated and Confer Sterile Immunity against Infection," *Infect Immun.* Aug. 2007; 75(8):3758-3768, American Society for Microbiology, United States (2007).
Long, C.A. and Hoffman, S.L., "Malaria-from Infants to Genomics to Vaccines," *Science* 297:345-347, American Association for the Advancement of Science, United States (2002).
Luke, T.C. and Hoffman, S.L., "Rationale and plans for developing a non-replicating, metabolically active, radiation-attenuated *Plasmodium falciparum* sporozoite vaccine," *The Journal of Experimental Biology* 206:3803-3808, The Company of Biologists Ltd, England (2003).
Mattig, F.R., et al., "A simple method for the purification of *Eimeria tenella* sporozoites," *Appl. Parasitol.* 34:139-142, Gustav Fischer Verlag Jena, Germany (1993).
Ménard, R., "Knockout malaria vaccine?" *Nature* 433:113-114, Nature Publishing Group, England (2005).
Mueller, A-K., et al., "Genetically modified *Plasmodium* parasites as a protective experimental malaria vaccine," *Nature* 433:164-167, Nature Publishing Group, England (2005).
Mueller, A-K., et al., "Plasmodium liver stage developmental arrest by depletion of a protein at the parasite-host interface," *Proc. Natl. Acad. Sci. USA.* 102(8):3022-3027, The National Academy of Sciences, United States (2005).
Nussenzweig, R.S., et al., "Protective Immunity produced by the Injection of X-irradiated Sporozoites of *Plasmodium berghei*," *Nature* 216:160-162, Nature Publishing Group, England (1967).
Nussenzweig, R., "Use of Radiation-attenuated Sporozoites in the Immunoprophylaxis of Malaria," *International Journal of Nuclear Medicine and Biology* 7:89-96, Pergamon Press Ltd, England (1980).
Ockenhouse, C.F., et al., "Phase I/IIa Safety, Immunogenicity, and Efficacy Trial of NYVAC-Pf7, a Pox-Vectored, Multiantigen, Multistage Vaccine Candidate for *Plasmodium falciparum* Malaria," *The Journal of Infectious Diseases* 177:1664-1673, The University of Chicago, United States (1998).
Plowe, C.V., et al., "The Potential role of vaccines in the elimination of falciparum malaria and the eventual eradication of malaria," *J. Infect. Dis.* 200:1646-1649, Oxford University Press, United States (2009).
Pombo, D.J., et al., "Immunity to malaria after administration of ultra-low doses of red cells infected with *Plasmodium falciparum*," *The Lancet* 360(9333):610-617, Lancet Publishing Group, England (2002).
Purcell et al., "Chemical attenuation of *Plasmodium berghei* sporozoites induces sterile immunity in mice," *Infect. Immun.* 76:1193-1199, American Society for Microbiology, United States (2008).
Purcell et al., "Chemically attenuated *Plasmodium* sporozoites induce specific immune responses, sterile immunity, and cross-protection against heterologous challenge," *Vaccine* 26(38): 4880-4884, National Institutes of Health, United States (2008).
Rénia, L., et al, "Vaccination against malaria with live parasites," *Expert Rev. Vaccines* 5:473-481, Future Drugs Ltd, United Kingdom (2006).
Rénia L., "Protective immunity against malaria liver stage after vaccination with live parasites," *Parasite* 15(3):379-83 (2008).
Richie, T.L. and Saul, A., "Progress and challenges for malaria vaccines," *Nature* 415:694-701, Macmillan Magazines Ltd, England (2002).
Rieckmann, K.H., "Human immunization with attenuated sporozoites," *Bulletin of the World Health Organization* 68 (Suppl.):13-16, World Health Organization, Switzerland (1990).
Roestenberg, M.D., "Protection against Malaria Challenge by Sporozoite Inoculation," *New England Journal of Medicine* 361(5):468-476, Massachusetts Medical Society, United States (2009).
Sedegah et al., "Cross-protection between attenuated *Plasmodium berghei* and *P. yoelii* sporozoites," *Parasite Immunology* 29:559-565, Blackwell Publishing Ltd, United States (2007).
Spitalny, G.L. and Nussenzweig, R.S., "Effect of Various Routes of Immunization and Methods of Parasite Attenuation on the Development of Protection Against Sporozoite-Induced Rodent Malaria," *Proceedings of the Helminthological Society* 39 (Special Issue):506-514, United States (1972).
Trager, W. and Jenen, J.B., "Continuous Culture of *Plasmodium Falciparum*: its.Impact on Malaria Research," *International Journal for Parasitology* 27(9):989-1006, Elsevier Science Ltd., Great Britain (1997).
Vanbuskirk et al., "Preerythrocytic, live-attenuated *Plasmodium falciparum* vaccine candidates by design," *Proc. Natl. Acad. Sci. USA.* 106(31):13004-13009, The National Academy of Sciences, United States (2009).
Van Dijk et al., "Genetically attenuated, P36p-deficient malarial sporozoites induce protective immunity and apoptosis of infected

(56) References Cited

OTHER PUBLICATIONS liver cells," *Proc. Natl. Acad. Sci. USA.* 102(34):12194-12199, The National Academy of Sciences, United States (2005).
Van Schaijk et al., "Gene disruption of *Plasmodium falciparum* p52 results in attenuation of malaria liver stage development in cultured primary human hepatocytes," *PLoS One* 3(10):e3549 (2008).
Warburg, A. and Miller, L.H., "Sporogonic Development of a Malaria Parasite In Vitro," *Science* 255(5043):448-450, American Association for the Advancement of Science, United States (1992).
Warburg, A., et al., "In vitro culture of the mosquito stage of *Plasmodium falciparum*," *Experimental Parasitology* 76(2):121-126, Academic Press, Inc., United States (1993).
Waters, A.P., et al., "Malaria Vaccines: Back to the Future?," *Science* 307:528-530, AAAS, United States (2005).
Wood, D.E., et al., "The Use of Membrane Screen Filters in the Isolation of *Plasmodium berghei* Sporozoites from Mosquitos," *Bulletin of the World Health Organization* 57(Suppl. 1):69-74 (1979).
Wykes, M. and Good M.F., "A case for whole-parasite malaria vaccines ," *Int. J. Parasitol.* 37:705-712, Academic Press, Inc., United States (2007).
The Notification of Transmittal of the International Search Report and Written Opinion of the International Searching Authority issued in Int'l Patent Application No. PCT/US2010/20564, 12 pages, mailed Mar. 9, 2010.
Supplementary European Search Report and Opinion for EP Application No. 10731974.1, Munich, Germany, mailed on Aug. 14, 2012.
Office Action mailed Sep. 13, 2010, in U.S. Appl. No. 12/684,863, Sim, B.K.L., et al., filed Jan. 8, 2010.
Office Action mailed Apr. 19, 2011, in U.S. Appl. No. 12/684,863, Sim, B.K.L., et al., filed Jan. 8, 2010.
Office Action mailed Feb. 6, 2012, in U.S. Appl. No. 12/870,102, Sim, B.K.L., et al., filed Aug. 27, 2010.
Office Action mailed Nov. 6, 2013, in U.S. Appl. No. 13/730,294, Graser, J. E., et al., filed Dec. 28,2012.
Arevalo-Herrera, M., et al., "*Plasmodium vivax* malaria vaccine development," *Molecular Immunology* 38(6):443-455, Elsevier Science Ltd. (2001).
Bojang, K.A., et al , "Efficacy of RTS,S/AS02 malaria vaccine against *Plasmodium falciparum* infection in semi-immune adult men in The Gambia: a randomized trial," *Lancet* 358(9297):1927-1934 (2001).
Clyde, D.F., et al , "Immunization of Man Against Sporozoite-Induced Falciparum Malaria," *Am. J. Med. Sci.* 266:169-177 (1973).
Clyde, D.F., et al., "Specificity of Protection of Man Immunized Against Sporozoite-Induced Falciparum Malaria," *Am. J. Med. Sci.* 266:398-401 (1973).
Collins, W.E., et al., "Adaptation of a strain of *Plasmodium vivax* from Mauritania to New World monkeys and Anopheline Mosquitoes," *J. Parasitol.* 84:619-621, American Society of Parasitologists (1998).
Collins, W.E., et al., "Potential of the Panama strain of *Plasmodium vivax* for the testing of malarial vaccines in *Aotus nancymai* monkeys," *Am. J. Trop. Med. Hyg.* 67:454-458, American Society for Tropical Medicine and Hygiene (2002).
Egan, J.E., et al., "Humoral immune responses in volunteers immunized with irradiated *Plasmodium falciparum* sporozoites," *J. Trop. Med. and Hygiene.* 49:166-173(1993).
Food and Drug Administration, "Guidance for Industry, Content and Format of Chemistry, Manufacturing and Controls Information and Establishment Description Information for a Vaccine or Related Product," http://www.fda.gov/cber/guidelines.htm, (1999).
Garfield, R.M. and Vermund, S.H., "Changes in Malaria Incidence After Mass Drug Administration in Nicaragua," *The Lancet* 322:500-503, Elsevier, UK (1983).
Gerberg, E.J., "Manual for Mosquito Rearing and Experimental Techniques," American Mosquito Control Association, Inc., Bulletin No. 5 (1979).

Grady et al., "Program and Abstracts of the 41st Annual Meeting of the American Society of Tropical Medicine and Hygiene," Supplement to *The American Journal of Tropical Medicine and Hygiene* 47(4): 218 (1992), Abstract only.
Hamilton, D.R., et al.,"An Integrated System for Production of Gnotobiotic *Anopheles quadrimaculatus*," *Journal of Invertebrate Pathology* 30:318-324, Academic Press, New York and London (1977).
Hurd, H., et al., "In vitro methods for culturing vertebrate and mosquito stages of Plasmodium," *Microbes and Infection* 5:321-327, Editions scientifiques et medicales Elsevier SAS, France (2003).
Hurtado et al., "Regular production of infective sporozoites of *Plasmodium falciparum* and *P. vivax* in laboratory-bred *Anopheles albimanus*," *Anals. Trop. Med. & Parasit.* 91:49-60 (1997).
Kester, K.E., et al., "Efficacy of recombinant circumsporozoite protein vaccine regimens against experimental *Plasmodium falciparum* malaria," *J. Infect. Dis.* 183:640-7 (2001).
Li, X., et al., "Design of a potent CD1d-binding NKT cell ligand as a vaccine adjuvant," *PNAS* 107(29):13010-13015 (2010).
Lin, K., et al., "In Vivo Protection Provided by a Synthetic New Alpha-Galactosyl Ceramide Analog against Bacterial and Viral Infections in Murine Models," *Antimicrobial Agents and Chemotherapy* 54(10): 4129-4136, American Society for Microbiology, United States (2010).
Malik, A., et al., "Human cytotoxic T lymphocytes against the *Plasmodium falciparum* circumsporozoite protein." *Proc. Natl. Acad. Sci.* 88:3300-3304, National Academy of the Sciences, United States (1991).
Miller, L., et al., "Research toward vaccines against malaria," *Nature Medicine Vaccine Supplement*, 4(5):520-524, Nature America Inc., United States (1998).
Munderloh, U.G., et al., "*Anopheles stephensi* and *Toxorhynchites amboinensis*: aseptic rearing of mosquito larvae on cultured cells," *J. Parasit.* 68:1085-91 (1982).
Munderloh, U.G., et al., "Malarial Parasites Complete Sporogony in Axenic Mosquitoes," *Experientia* 41:1205-1207, Birkhäuser Verlag AG (1985).
Okiro, E.A., et al., "The decline in paediatric malaria admissions on the coast of Kenya," *Malaria Journal* 6:151:1-11, BioMed Central, UK (2007).
Padte, N., et al., "Clinical development of novel CD1d-binding NKT cell ligand as a vaccine adjuvant," *Clinical Immunology* 140: 142-151, Elsevier Ltd., United States (2011).
Rieckmann, K., et al, "Sporozoite Induced Immunity in Man Against an Ethiopian Strain of *Plasmodium Falciparum*," *Royal Society of Tropical Medicine and Hygiene* 68:258-259 (1974).
Rosales-Ronquillo, M.C., et al., "Aseptic Rearing of *Anopheles stephensi*," *Annals of the Entomological Society of America*. 66:949-954, Entomological Society of America (1973).
Schofield, L., et al., "Synthetic GPI as a candidate anti-toxic vaccine in a model of malaria," *Nature*. 418:785-789, Nature Publishing Group (2002).
Schuster, F., "Cultivation of *Plasmodium* spp.," *Clinical Microbiology Reviews*. 15(3):355-364, American Society for Microbiology, United States (2002).
Smith, D.L., et al., "Revisiting the Basic Reproductive Number for Malaria and Its Implications for Malaria Control," *PLoS Biology*. 5:0531-0542, www.plosbiology.org, United States (2007).
Stoute, J.A., et al., "Long term efficacy and immune responses following immunization with the RTS, S malaria vaccine." *J. Infect. Dis.* 178:1139-1144 (1998).
Tsuji, M. et al., "Progress toward a Malaria Vaccine: Efficient Induction of Protective Anti-Malaria Immunity," *Biol. Chem.* 382(4):553-570, Walter de Gruyter, Berlin and New York (2001).
Vanderberg, J.P., "Development of Infectivity by the *Plasmodium berghei* Sporozoite," *The Journal of Parasitology* 61(1):43-50, The American Society of Parasitologists (1975).
Wu, Y., et al., "Phase 1 Trial of Malaria Transmission Blocking Vaccine Candidates Pfs25 and Pvs25 Formulated with Montanide ISA 51," *PLoS Biology* 3:1-9, www.plosbiology.org, United States (2008).

(56) References Cited

OTHER PUBLICATIONS

Zapata, J.C., et al., "Reproducible infection of intact *Aotus lemurinus* griseimembra monkeys by *Plasmodium falciparum* sporozoite inoculation," *J. Parasitol.* 88:723-729, American Society of Parasitologists (2002).
Esp@cenet Database, English language abstract of CN1142887A, published Dec. 18, 1995 (listed as document FP6 on the accompanying form PTO/SB/08a equivalent).
Esp@cenet Database, English language abstract of CN1213497A, published Oct. 8, 1997 (listed as document FP7 on the accompanying form PTO/SB/08a equivalent).
Office Action mailed Jul. 14, 2014, in U.S. Appl. No. 13/730,281, Sim, B.K.L., et al., filed Dec. 28, 2012.
Moser, G., et al., "Sporozoites of Rodent and Simian Malaria, Purified by Anion Exchangers, Retain their Immunogenicity and Infectivity," *J. Protozool.* 25(1):119-124, Blackwell Publishing Ltd. (1978).
Notice of Allowance mailed Sep. 18, 2015 in U.S. Appl. No. 14/671,003, Sim, B.K.L., et al., filed Mar. 27, 2015.
Notice of Allowance mailed Jul. 27, 2011, in U.S. Appl. No. 12/684,863, Sim, B.K.L., et al., filed Jan. 8, 2010.
Notice of Allowance mailed Oct. 1, 2012, in U.S. Appl. No. 12/870,102, Sim, B.K.L., et al., filed Aug. 27, 2010.
Notice of Allowance mailed Jun. 23, 2014, in U.S. Appl. No. 13/730,294, Graser, J. E., et al., filed Dec. 28,2012.
Notice of Allowance mailed Nov. 25, 2014, in U.S. Appl. No. 13/730,281, Sim, B.K.L., et al., filed Dec. 28, 2012.

PURIFIED PLASMODIUM AND VACCINE COMPOSITIONS

CROSS REFERENCE TO RELATED APPLICATIONS

This invention was developed in part under the auspices of an agreement between Sanaria, Inc. (Dr. Stephen L. Hoffman—CEO) and Protein Potential, Inc. (Dr. Kim Lee Sim—President) and is entitled to the benefits of the CRE-ATE Act of 2004. This application is a continuation application of U.S. Ser. No. 14/671,003, filed Mar. 27, 2015, now granted U.S. Pat. No. 9,241,982, which is a continuation application of U.S. Ser. No. 13/730,281, filed Dec. 28, 2012, now granted U.S. Pat. No. 8,992,944, which is a divisional application of U.S. Ser. No. 12/870,102, filed Aug. 27, 2010, now granted U.S. Pat. No. 8,367,810, which is a divisional application of U.S. Ser. No. 12/684,863, filed Jan. 8, 2010, now granted U.S. Pat. No. 8,043,625, which claims priority to U.S. Ser. No. 61/202,001, filed Jan. 16, 2009, each of which are incorporated herein by reference.

BACKGROUND OF THE INVENTION

Field of the Invention

This application relates to purification of eukaryotic pathogens and parasites, particularly, *Plasmodium* sporozoite-stage parasites. More particularly it relates to substantially pure parasites and methods of preparing and using them. The application also relates to vaccine and pharmaceutical compositions of purified sporozoite stage *Plasmodium* parasites, both attenuated and non-attenuated, and methods of using the compositions in vaccines and other preparations to prevent malaria and other diseases, treat diseases, and as a means to infect volunteers in the testing of malaria vaccines and drugs.

Background Art

Malaria is a disease that is estimated to affect 300-500 million people and kills 1-3 million individuals annually. It also has an enormous economic impact on people in the developing world, especially those in sub-Saharan Africa. *Plasmodium falciparum* accounts for the majority of deaths from malaria in the world. The World Tourist Organization reported that of the nearly 700 million international tourist arrivals recorded worldwide in 2000, approximately 9 million were to West, Central or East Africa, 37 million were to South-East Asia, 6 million to South Asia and 10 million to Oceania. It is estimated that more than 30,000 travelers from North America, Europe, and Japan contract malaria per year. For more than 100 years during every military campaign conducted where malaria was transmitted, U.S. forces have had more casualties from malaria than from hostile fire. An estimated 12,000,000 person days were lost during World War II and 1.2 million during the Vietnam conflict due to malaria.

Transmission of the *Plasmodium* parasite occurs through the bite and feeding of infected female *Anopheles* mosquitoes which are active from dusk to dawn. *Plasmodium*, at the sporozoite stage of development, migrate from the bite site to the liver, primarily via the blood stream, where they multiply within hepatocytes, producing, in the case of *P. falciparum*, about 10,000-40,000 progeny per infected cell. These liver stage parasites express some proteins which are not expressed at the sporozoite stage. At this stage, parasites re-enter the blood stream as merozoites, expressing some proteins which are different from those expressed during the sporozoite and early hepatic stages, and invade erythrocytes, where additional multiplication increases parasite numbers by approximately 10 to 20 fold every 48 hours. Unlike the five to ten day development in the liver, which does not induce any symptoms or signs of malaria, untreated blood stage infection causes hemolysis, shaking chills, high fevers, and prostration. In the case of *P. falciparum*, the most dangerous of the four major species of *Plasmodium* that cause human disease (*P. vivax, P. malariae*, and *P. ovale [P. knowlesi* can also cause human disease]), the disease is complicated by disruption of microcirculatory blood flow and metabolic changes in vital organs such as the brain, kidneys and lungs, frequently leading to death if not urgently treated.

An effective vaccine against *P. falciparum* malaria remains one of the great challenges of medicine. Despite over one hundred years of effort, hundreds of millions of dollars in research, lifelong sacrifice from dedicated physicians and scientists, and many promising experimental vaccines, there is no marketed vaccine to alleviate one of the great infectious scourges of humanity.

A generation ago, public health initiatives employing chloroquine, DDT and vector control programs seemed poised to consign *falciparum* malaria to insignificance as a worldwide menace. The lack of an effective vaccine complicated these efforts, but sustainable control seemed imminent.

The promise of impending success was short-lived and the reasons for failure were multi-factorial. The parasites grew increasingly resistant to highly effective and affordable anti-malarial medications, vector control measures lapsed, and trans-migration, war and economic disruption became increasingly more common in endemic areas of the developing world. As a result, *P. falciparum* malaria resurged, annually placing at least 2.5 billion humans at risk, causing 300-900 million infections, and killing 1-3 million people. Of the many social, economic, environmental and political problems that afflict the developing world, *P. falciparum* malaria is increasingly seen as both a root cause and cruel result of these inequities, and is a singular impediment to solving these complex problems. Controlling *P. falciparum* malaria in the developing world may not be possible without an effective vaccine. In practice, given social, political and economic realities, we believe that a vaccine may be an essential component of a sustainable control program, and will be required for a global eradication campaign.

During the last 25 years most research effort has been spent on identifying the antigenic subunits of the parasite which confer immunity—unfortunately, with less than satisfying results. This effort and the attendant difficulties in developing a suitable vaccine have been described (Nussenzweig V., F. and R. S. Nussenzweig, *Adv. Immunol.*, (1989) 45: 283-334; Hoffman S. L. et al. In: Hoffman S. L., ed. *Malaria Vaccine Development: A Multi Immune Response Approach* (1996) Washington, D.C.: ASM Press, pp. 35-75; Hoffman S. L. and L. H. Miller, In: Hoffman S. L., ed. *Malaria Vaccine Development: a Multi-Immune Response Approach*. (1996) Washington, D.C.: ASM Press, pp. 1-13; Epstein, J. E. et al, *Curr. Opin. Mol. Ther.* (2007) 9:12-24; Richie, T. L. & A. Saul, *Nature*, (2002) 415:694-701).

There are continuing efforts to produce subunit malaria vaccines. Typical of such attempts, Paoletti et al. (U.S. Pat. No. 5,766,597, issued Jun. 16, 1998) disclose a recombinant poxvirus containing DNA from *Plasmodium* coding for one or more circumsporozoite proteins, including an embodiment termed NYVAC-Pf7, possibly useful as a potential malaria vaccine. Subsequent testing of this construct proved to be disappointing (Ockenhouse, C. F. et al. *J. Infect. Dis.* (1998) 177: 1664-73).

Similarly, another candidate subunit circumsporozoite vaccine was proposed and identified as RTS, S/AS02A (Stoute J. A. et al. J. Infect. Dis. (1998) 178: 1139-44). The results of the first Phase 2b field trial of this vaccine in one-four year old children in Mozambique was reported (Alonso, P. L. et al. Lancet (2004) 364:1411-1420; Alonso, P. L. et al. Lancet (2005) 366:2012-2018; Epstein, J. E. et al, Supra; Richie, T. L., F. & A. Saul, Supra), as were the results of other Phase 2b field trials in infants (Aponte, J. J. et al. (2007) The Lancet 370:1543-1551; Bejon, P. et al (2008) NEJM 359:2521-32; Abdullah, S et at (2008) NEJM 359: 2533-44. The vaccine has demonstrated modest protective efficacy.

On the other hand, the demonstration of the effectiveness of whole parasite, radiation attenuated sporozoites (delivered to human hosts by mosquito exposure and to animal hosts by intravenous (i.v.) inoculation) in conferring high levels of protective immunity when recipients are subsequently challenged with pathogenic parasites (most importantly attenuated *Plasmodium falciparum* to human hosts) was an early milestone in the quest for a suitable vaccine (Hoffman S. L. et al., J. Infect. Dis. (2002) 185: 1155-64). Eventually, this led to efforts to explore the technical hurdles which present themselves in transforming these earlier observations into a practical vaccine approach comprising aseptic attenuated sporozoites (Luke, T. C.& S. L. Hoffman, J. ExP. Biol., (2003) 206:3803-3808; Hoffman, S. L., and T. C. Luke U.S. Pat. No. 7,229,627 and U.S. Publication 2005/0208078). It has also led to increased interest generally in the utility of vaccines utilizing attenuated sporozoites (Menard, R., Nature 2005) 433:113-114; Waters, A. P. et al. Science. (2005) 307:528-530; Wykes, M. F. & M. F. Good, Int. J. Parasitol. (2007) 37:705-712; Renia, L. et al, Expert Rev. Vaccines, (2006) 5:473-481; Epstein, J. E. et al, Supra).

Other modes of attenuation have also been demonstrated. For example, It was shown that attenuated sporozoites resulting from gene alteration of *Plasmodium berghei* protects mice against *P. berghei* malaria (Kappe et al. U.S. Pat. No. 7,122,179; Mueller et al. Nature (2005); Mueller, et al. PNAS (2005); van Dijk et al. PNAS (2005) 102:12194-12199); Waters, U.S. Pat. No. 7,550,138; Labaied et al. Infect. And Immun. (2007). Recently genetic attenuation of the sporozoites of *P. falciparum* has be disclosed (van Schaijk et al. PLoS ONE (2008) 3:e3549); VanBuskirk et al. PNAS.

Similarly, chemical attenuation of *Plasmodium* has be described (Purcell et al. Infect. Immun. (2008)76:1193-99; Purcell et al Vaccine (2008) 26:4880-84).

Others have also described methods of culturing unpurified preparations of sporozoites and inducing parasite differentiation to axenic liver stages (Kappe et al. US Pub. 2005/0233435).

The studies discussed above set forth certain limitations. For example, while sporozoites delivered to human hosts by the bite of a mosquito generate an effective immune response against malaria, such a method of delivery is clearly not a practical method for vaccinating a population in need of protection against malaria. Additional studies in mice, referred to above, have suggested that the delivery of attenuated sporozoites to mice intravenously are also effective, whereas other means of delivery (e.g., intramuscular) in comparison, are not. An intravenous delivery method, however, is also not practical if a malarial vaccine is to be delivered to numerous individuals (including children and the elderly). Intravenous delivery has increased risks, increased costs, and patients are far less likely to agree to be vaccinated using such a method. Thus, there was a need in the art to provide an effective malarial vaccine that provides protective immunity, where the vaccine can be administered by a variety of methods.

With regard to considerations for human vaccines, the purity of the immunogen and the presence or absence of non-specific, attendant material which may be immunogenic or toxic are further essential issues which have not previously been resolved. Isolated attenuated sporozoite preparations, as used in studies discussed above, contain contaminating and other attendant material. There was a need in the art to develop sporozoite-based vaccines, particularly in humans, that employ aseptically prepared, sterile, purified preparations of sporozoites for use in vaccine compositions. Such aseptically prepared, purified preparations of sporozoites may also be more effective than non-purified preparations when such preparations are administered by non-intravenous delivery methods. (e.g., intramuscular, intraperitoneal, intradermal, epidermal, mucosal, submucosal, cutaneous, or subcutaneous).

BRIEF SUMMARY OF THE INVENTION

Disclosed are compositions of live, infectious, substantially purified sporozoites, particularly *Plasmodium* sporozoites—attenuated sporozoites as well as pathogenic sporozoites. Also disclosed are methods of making live, infectious, substantially purified parasites and methods of using compositions of substantially purified attenuated sporozoites as vaccines to prevent malaria. Also disclosed are methods of using purified pathogenic parasites useful for assessing the effectiveness of antimalarial drugs and vaccines, and in conjunction with antimalarial agents such as chloroquine, useful for conferring protective immunity.

In an embodiment, methods of using aseptically produced, sterile, infectious, substantially purified, attenuated *Plasmodium* sporozoites to confer protective immunity against malaria in human and other mammalian hosts are provided. Such methods and compositions can be used to confer protective immunity against malaria caused by *P. falciparum* and other *Plasmodium* species, without complications which may result from the use of unpurified preparations.

In an embodiment compositions of substantially purified pathogenic *Plasmodium* sporozoites and methods of using them as research tools, in clinical testing, and in prophylactic vaccination regimens are provided.

Compositions of live, infectious, attenuated, substantially purified sporozoites, as well as dosages, regimens and routes of administration to human and other mammalian subjects are provided.

In an embodiment purified *Plasmodium* parasites in excipient are provided, particularly parasites at the sporozoite stage of development, said parasites metabolically active, infectious, and substantially free from contaminant material. In another embodiment, the sporozoites are aseptically prepared. In another embodiment, the sporozoites are sufficiently attenuated to prevent development beyond the liver stage (mature schizont stage) of the parasite life cycle.

In another embodiment, methods are provided for conferring protective immunity in mammalian and human hosts against malaria caused by a *Plasmodium* species, comprising providing live, metabolically active, infectious, attenuated sporozoites of a *Plasmodium* species in an excipient and substantially free of attendant material and administering at least one dose of said sporozoite preparation to said host; wherein pathological manifestations of malaria are prevented and the host is protected from developing malaria after subsequent exposure to pathogenic *Plasmodium* sporozoites of said species.

In another embodiment, methods are provided for purifying metabolically active, infectious parasites, particularly *Plasmodium* sporozoites by providing an aqueous pre-purification preparation comprising sporozoites and attendant non-sporozoite material, sequentially passing the preparation through a set of size exclusion filters comprising: a) a first exclusion filter with a nominal pore size capable of retaining attendant material larger than 10 microns and allowing passage of the sporozoites; b) a second exclusion filter with a nominal pore size capable of retaining attendant material larger than about 0.6 microns and allowing passage of the sporozoites; and c) a third size exclusion membrane filter with a precise pore size capable of retaining substantially all attendant material larger than 1.2 microns and allowing passage of the sporozoites. Substantially purified sporozoites are then collected on a collecting filter with a pore size capable of retaining the sporozoites, and the purified sporozoite preparation is then eluted from the collecting filter and resuspended at the desired concentration.

In another embodiment, compositions useful for determining the efficacy of malaria-related drugs, vaccines and the like are provided. The compositions comprise live, substantially purified, pathogenic *Plasmodium* parasites.

BRIEF DESCRIPTION OF THE DRAWINGS/FIGURES

FIG. 1a—Photo-micrographic observation of crude preparations of PfSPZ (Campaign 3). Photo-micrographs taken at 200× magnification. Before Purification SGM=837 ng/25,000 PfSPZ (Samples were adjusted to 15×10$^6$ PfSPZ/ml)

Figure 1B:
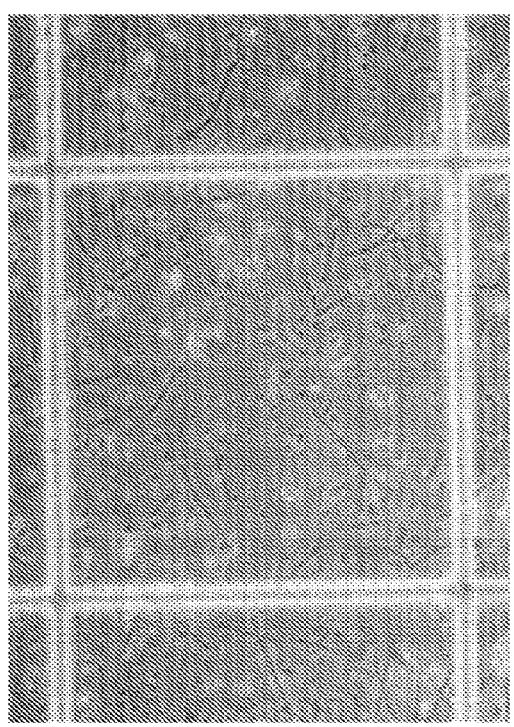

FIG. 1b—Photo-micrographic observation of purified preparations of PfSPZ (Campaign 3). Photo-micrographs taken at 200× magnification. After Purification SGM=0.23 ng/25,000 PfSPZ (Samples were adjusted to 18×10$^6$ PfSPZ/ml)

Figure 2A:
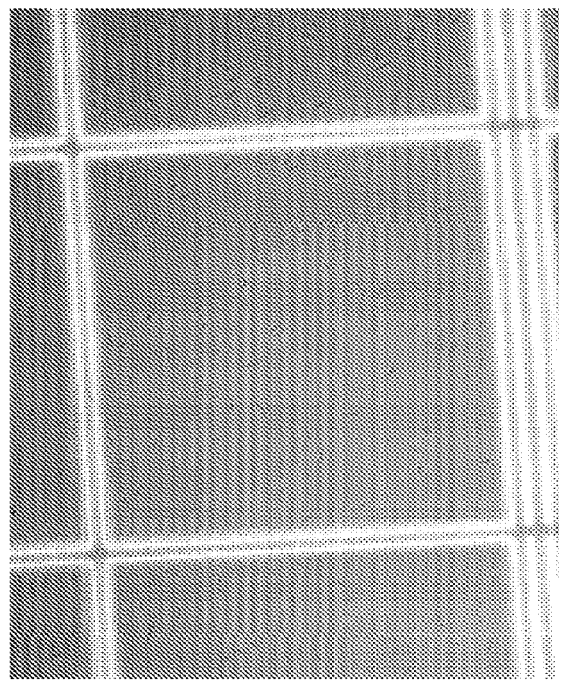

FIG. 2a—Photo-micrographic observation of crude preparations of PfSPZ (Campaign 6). Photo-micrographs taken at 200× magnification. Before Purification— SGM=781 ng/25,000 PfSPZ (Samples were adjusted to 17.78×10$^6$ PfSPZ/ml)

Figure 2B:
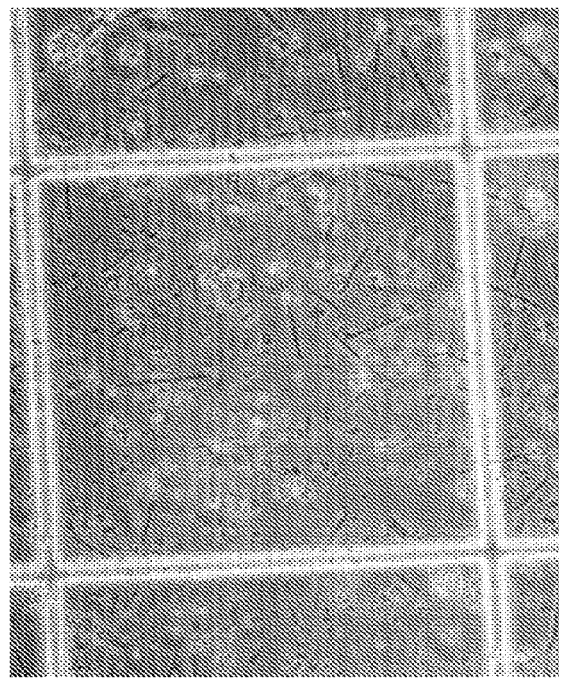

FIG. 2b—Photo-micrographic observation of purified preparations of PfSPZ (Campaign 6). Photo-micrographs taken at 200× magnification. After Purification—SGM=0.65 ng/25,000 PfSPZ (Samples were adjusted to 16.71×10$^6$ PfSPZ/ml)

Figure 3C:
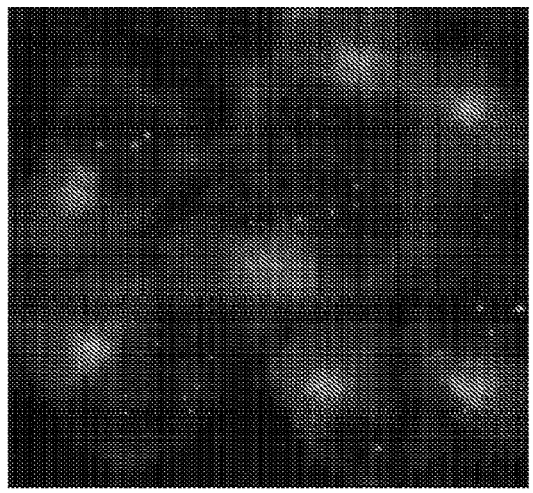
Figure 3B:
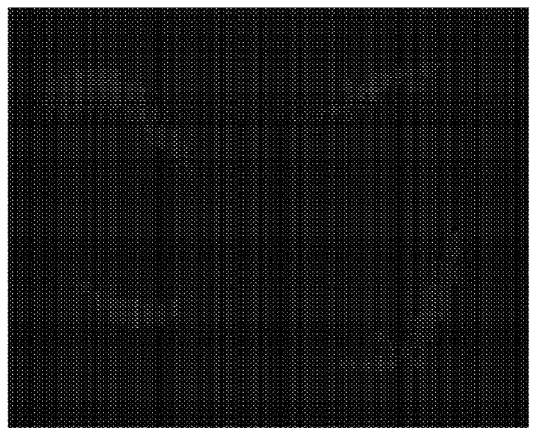
Figure 3A:
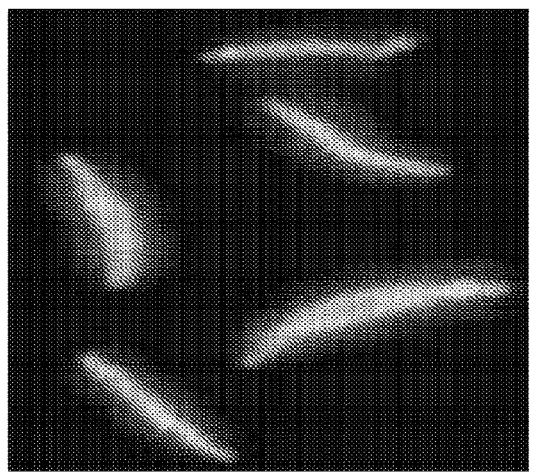

FIG. 3a—Stage specific expression of PfLSA-1 (*P. falciparum* sporozoites). PfSPZ incubated with an anti-PfCSP monoclonal antibody.

FIG. 3b—Stage specific expression of PfLSA-1 (*P. falciparum* sporozoites). PfSPZ incubated with anti-PfLSA-1 polyclonal antibodies.

FIG. 3c—Stage specific expression of PfLSA-1 (3 day liver stage parasites). 3 day liver stage parasites incubated with anti-PfLSA-1 polyclonal antibodies.

DETAILED DESCRIPTION OF THE INVENTION

There is presently no FDA-approved malaria vaccine. However, results published during the last 30 years have demonstrated that administration of radiation attenuated *P. falciparum* sporozoites delivered by the bite of greater than 1,000 *P. falciparum*-infected mosquitoes provides sterile protective immunity in greater than 90% of exposed individuals for at least 42 weeks, and was effective against multiple isolates of *P. falciparum* from throughout the world. As provocative as these observations might have been, they did not suggest a vaccine or an obvious approach to developing a malaria vaccine, because of several technical hurdles, including isolating and purifying sporozoites and doing so under aseptic conditions. Furthermore, work by a number of scientists indicated that excellent protection could only be achieved in the mouse model system by intravenous administration of attenuated sporozoites. Because parenteral non-intravenous routes of administration conventionally used in human immunization, e.g. subcutaneous and intramuscular inoculation, did not lead to adequate protective immunity in this mouse model system, it was not considered possible to develop an attenuated sporozoite vaccine for humans. Utilizing a mouse model system that is considered more analogous to human malaria caused by *P. falciparum*, it has been found that parenteral non-intravenous administration of sporozoites leads to high level protection (US Publication No. 2005/0208078). Many other technical hurdles of development for a pharmaceutically acceptable, live attenuated malaria vaccine have also been overcome— among them, aseptic production of sufficient quantities of sporozoites isolated from attendant material (See particularly, Hoffman, S L and T C Luke, U.S. Pat. No. 7,229,627 B2, explicitly incorporated herein by reference).

However, a vaccine suitable for routine use in human subjects requires a substantially pure inoculum and a sporozoite inoculum requires sporozoites that have been substantially purified from the source from which they were produced. The vaccine compositions provided herein comprise *Plasmodium* sporozoites in a substantially purified form, substantially free of attendant (source) material, which is not specific to the sporozoites themselves. Additionally, in some embodiments of vaccine compositions provided herein the vaccine compositions are substantially free from contaminating material, microorganisms and exogenous pathogens. Provided are substantially purified sporozoites and methods of purifying sporozoites, and compositions of purified sporozoites and excipient.

DEFINITIONS

The terms "about" or "approximately" means within one standard deviation as per the practice in the art.

"Additive" as used herein as a noun is a compound or composition added to a sporozoite preparation to facilitate preservation of the preparation. Additives may include cryoprotectants such as DMSO and glycerol, antioxidants, and the like.

"Aseptic" as used herein means absent the introduction of detectable contamination of other microorganisms such as bacteria, fungi, pathologic viruses and the like. An aseptic method of sporozoite preparation results in a sterile preparation of sporozoites—free of any other type of microorganism or infectious agent. Microbiological assays used to monitor an aseptic methodology assess the presence or absence of contamination. They include, but are not limited to, the Microbial Limits Test, current USP <61>, incorporated herein by reference.

"Attendant" material as used herein means material in a crude preparation of parasites which is not specific to the parasites per se. For example in a preparation of sporozoites, attendant material is that which is not specific to the sporozoite per se. Attendant material includes material specific to the source from which sporozoites were grown or produced, particularly biological debris, more particularly protein, said material isolated along with the sporozoites in a crude preparation. That which makes a preparation "crude" is the attendant material in the preparation, and with regard to sporozoites, includes material specific to the substrate from which the sporozoites have developed or from which the sporozoites have been isolated. With regard to sporozoites dissected from and isolated from the salivary glands of host mosquitoes, attendant material is the host material, host protein, salivary gland material, saliva and the like. Attendant material does not include components which have been intentionally added to a preparation, e.g., excipient, diluent, additives and the like. In some embodiments, a component of attendant material which has been removed from a crude preparation may be added back to the purified preparation to optimize sporozoite infectivity sporozoite immunogenicity, or sporozoite presentation to the host. Such added back material is not considered attendant as defined herein.

"Attenuate" as used herein means to render a live organism unable to complete its life cycle without killing it. The organism may have a limited capacity to replicate, express proteins, and to develop through some life cycle stages, but arrests development at a particular life cycle stage and is unable to developmentally progress beyond that stage. With regard to the attenuated *Plasmodium* parasites disclosed herein, i.e. parasites which have been exposed to radiation at the sporozoite stage, they retain the ability to infect host hepatocytes and express stage specific proteins, but are unable to develop beyond liver stage, are unable to reenter the blood stream of infected hosts subsequent to liver-stage (merozoite stage), are unable to cause the disease pathology of malaria. Other attenuated *Plasmodium*-species parasites may retain the ability to infect host hepatocytes, develop beyond liver stage, reenter the blood stream of infected hosts subsequent to liver-stage (merozoite stage), and even infect erythrocytes, but subsequently arrest development prior to the stage at which the disease pathology of malaria manifests itself.

"Conferring protective immunity" as used herein refers to providing to a population or a host (i.e., an individual) the ability to generate an immune response to protect against a disease (e.g., malaria) caused by a pathogen (e.g., *Plasmodium falciparum*) such that the clinical manifestations, pathology, or symptoms of disease in a host are reduced as compared to a non-treated host, or such that the rate at which infection, or clinical manifestations, pathology, or symptoms of disease appear within a population are reduced, as compared to a non-treated population.

"Contaminant" and contamination as used herein means adventitious microbial or viral contamination or pathogenic contamination, including but not limited to bacteria, viruses, *mycoplasma*, fungi and the like. An aseptic process is designed to prevent the introduction of contamination and a sterile preparation is absent the presence of contamination. Contaminants may be non-biologic or inorganic toxics as well. Contaminants may be accidentally or inadvertently introduced at any step during a process.

"Diluent" as used herein is a medium in which sporozoites and sporozoite compositions are prepared to achieve a desired concentration. Diluent may be, for example, normal saline or phosphate buffered saline, or media such as medium 199 or medium E199 (medium 199 with Earle's Balanced Salts).

"Excipient" means an inactive substance used as a carrier, vehicle, or diluent for the active ingredient of a pharmaceutical preparation such as a vaccine. As used herein, an excipient is an ingredient added to the preparation during the isolation and purification process to aid in the process, minimize non-specific interactions or adsorptions, and/or provide volume. Examples of excipients include inactive proteins such as serum albumins, particularly human serum albumin, from whatever source, including but not limited to purified from blood, produced as a recombinant protein or produced synthetically. Sporozoites dissected from mosquito salivary glands may be placed in excipient for further processing. Excipient may be added to pharmaceutical preparations for several reasons including, maintaining activity, increasing stability, or preventing inadvertent loss of isolated sporozoites throughout the purification process.

"Immune response" as used herein means a response in the recipient to the introduction of attenuated sporozoites generally characterized by, but not limited to, production of antibodies and/or T cells. Generally, an immune response may be a cellular response such as induction or activation of CD4+ T cells or CD8+ T cells specific for *Plasmodium* species epitopes, a humoral response of increased production of *Plasmodium*-specific antibodies, or both cellular and humoral responses. With regard to a malaria vaccine, the immune response established by a vaccine comprising sporozoites includes but is not limited to responses to proteins expressed by extracellular sporozoites or other stages of the parasite after the parasites have entered host cells, especially hepatocytes and mononuclear cells such as dendritic cells and/or to components of said parasites. In the instant invention, upon subsequent challenge by infectious organisms, the immune response prevents development of pathogenic parasites to the asexual erythrocytic stage that causes disease.

"Intravenous" as defined herein means intentional introduction, directly into the lumen of an identified large blood vessel such as a vein.

"Metabolically active" as used herein means alive, and capable of performing sustentative functions and some life-cycle processes. With regard to attenuated sporozoites this includes but is not limited to sporozoites capable of invading hepatocytes in culture and in vivo, potentially having a limited capacity to divide and progress through some developmental stages, and de novo expressing stage-specific proteins.

"Mitigate" as defined herein means to substantially reduce, or moderate in intensity, symptoms and/or pathology of malaria which might otherwise manifest subsequent to vaccination.

"Nominal" as defined herein and with regard to the pore size of a filter means the effective pore size and refers to the apparent pore size for passage of globular particles through the filter such that 90% of the particles of said size are excluded by the filter.

"Parenteral" as defined herein means not through the alimentary canal, but rather by introduction through some other route, as intradermal, subcutaneous, intramuscular, intraorbital, intracapsular, intraspinal, intrasternal, intravenous, transcutaneous and the like.

"Prevent" as defined herein and used in the context of preventing malaria means to keep a majority, up to all, of the pathology and clinical manifestations of malaria from manifesting.

"Purify" as defined herein and with regard to preparations of sporozoites, means to separate from attendant material or to separate from material considered to be undesirable.

"Sterile" as defined herein and with regard to sporozoites, means absent any contaminating microorganism. A sterile preparation of sporozoites is obtained by means of an aseptic preparation methodology. The sterility of a preparation is determined by specific assays, including but not limited to the Sterility Test current USP <71>, incorporated herein by reference.

"Substantially purified" with regard to a preparation of sporozoites means reduction in the amount of attendant contamination to less than 85 ng/25,000 sporozoites or at least an 18 fold reduction in attendant contamination. Satisfaction of either of the aforementioned criteria is sufficient to render a preparation of sporozoites "substantially purified."

"Therapeutic" as defined herein relates to reduction of clinical manifestations or pathology which have already become manifest. A "therapeutically effective amount" as used herein means an amount sufficient to reduce the clinical manifestations, pathology, or symptoms of disease in an individual, or an amount sufficient to decrease the rate at which clinical manifestations, pathology, or symptoms of disease appear within a population.

"Vaccine" as used herein is a preparation comprising an immunogenic agent and a pharmaceutically acceptable diluent potentially in combination with excipient, adjuvant and/or additive or protectant. The immunogen may be comprised of a whole infectious agent or a molecular subset of the infectious agent (produced by the infectious agent, synthetically or recombinantly). When the vaccine is administered to a subject, the immunogen stimulates an immune response that will, upon subsequent challenge with infectious agent, protect the subject from illness or mitigate the pathology, symptoms or clinical manifestations caused by that agent. A therapeutic (treatment) vaccine is given after infection and is intended to reduce or arrest disease progression. A preventive (prophylactic) vaccine is intended to prevent initial infection or reduce the rate or burden of the infection. Agents used in vaccines against a parasitic disease such as malaria may be whole-killed (inactive) parasites, live-attenuated parasites (unable to fully progress through their life cycle), or purified or artificially manufactured molecules associated with the parasite—e.g. recombinant proteins, synthetic peptides, DNA plasmids, and recombinant viruses or bacteria expressing *Plasmodium* proteins. A vaccine may comprise sporozoites along with other components such as excipient, diluent, carrier, preservative, adjuvant or other immune enhancer, or combinations thereof, as would be readily understood by those in the art.

Purification of Sporozoites

*Plasmodium*-species parasites are grown aseptically in cultures as well as in vivo in *Anopheles*-species mosquito hosts, most typically *Anopheles stephensi* hosts. Methods of axenically culturing *Plasmodium*-species liver stage parasites (Kappe et al. US Pub. 2005/0233435) and methods of producing attenuated and non-attenuated *Plasmodium*-species sporozoites, particularly, methods of growing and attenuating parasites in mosquitoes, and harvesting attenuated and non-attenuated sporozoites are known in the art and have been described (See, Hoffman & Luke, U.S. Pat. No. 7,229,627; US Pub. No. 2005/0220822.

The purification aspect of the invention separates sporozoites from attendant material such as mosquito host salivary gland material (hereinafter, "SGM"), mosquito-specific material, and any other non-sporozoite material or component, thereby achieving a substantially purified preparation containing sporozoites. As an aspect of purification, sporozoites are concentrated relative to attendant contaminating material such as SGM. Here, the purity of a preparation is measured using an enzyme-linked immunosorbent assay (ELISA) to quantify attendant antigenic SGM present in crude and purified preparations of sporozoites (hereinafter, "SGM-ELISA"). Other methods, such as, but not limited to, capillary electrophoresis, mass spectrometry, reverse phase chromatography, immunoblotting, light-scattering and UV spectrometry, may be similarly adapted to measure attendant material. With regard to the purification of sporozoites from sources other than mosquitoes, similar assays, such as ELISA, relevant to the attendant material in the crude preparation from which sporozoites are to be purified, would be similarly adapted. The development of such ELISA assays adapted to antigens of attendant material from sources other than mosquito salivary glands would use a similar protocol, commonly known to those in the art. To illustrate, a protocol for an impurity assay of attendant SGM is provided. It is to be understood that this protocol is provided for illustration and may be modified e.g. by scaling up, or otherwise modified, and is not intended to limit the scope of the invention as claimed.

Purification Methods

Disclosed herein are methods of purifying live *Plasmodium* species, e.g. *falciparum, vivax, malariae,* or *ovale*.

The methods disclosed utilize a series of size exclusion filters of different types and with different pore sizes, assembled in a novel and non-obvious fashion. The methodology eliminates attendant material from preparations of live, motile parasites. An aspect of this method is that the pore size of a size exclusion filter in sequence is not always smaller than the pore size of the size exclusion filter which precedes it. Another aspect is that some filters provide a matrix with a nominal pore size and at least one filter provides a track-etched filter with a precise pore diameter. At least one filter has a pore size close to or slightly smaller than the diameter of the parasite.

By way of example, the purification of *Plasmodium*-species sporozoites is disclosed; however, it will be understood by those practiced in the art that, based upon the physical size of the organism, adjustment of the filter pore size will yield a similar purification. For example, the *Plasmodium falciparum* sporozoite is rod-shaped, and about $0.8 \pm 0.2$ µm in diameter and $8.5 \pm 1.5$ µm in length. Hoffman, S L et al In Tropical Infectious Disease 2nd Ed. 2006, Elsevier, Philadelphia, Pa. pg 1027; Xu, L. H. et al 1985 Zoo. Res. 6:33-6.

Typically in a preparation for purification, the salivary glands from 150 to 400 mosquitoes are dissected. The sporozoites are released from the salivary glands by passage back and forth in a needle and syringe (trituration), and sporozoites from these glands are collectively purified. However, several fold more mosquitoes may be dissected in scaled up preparations, in an embodiment up to 1,000 mosquitoes, in another embodiment up to 5,000 mosquitoes, in another embodiment up to 10,000 mosquitoes. Sporozoites are released from salivary glands by trituration and the triturated salivary gland preparations (pre-purification preparations) are purified by the size exclusion filtration process disclosed herein. Sporozoites are maintained throughout the purification process in an excipient, typically one percent human serum albumin (HSA) in Medium 199 with Earle's salts (E-199).

A—Preparation of Material for Purification

The triturated dissection product (pre-purification preparation) is received altogether in a single tube at a time. This is the SGM pre-purification preparation. It represents about 100,000 to 1 billion sporozoites, preferably at least 1 million sporozoites and more preferably at least 25 million sporozoites. The measured amount of SGM in the pre-purification preparation is usually between 300 ng and 12,000 ng per 25,000 sporozoites, more typically, between 400 ng and 1,100 ng per 25,000 sporozoites. The pre-purification preparation is then diluted to 10 ml with excipient. Solutions and samples are kept between 15-30° C. for the duration of the purification.

B—Purification Procedure

Using a peristaltic pump the diluted pre-purification preparation is pumped across a series of size exclusion filters at a flow rate of at least 1 ml/min but no more than 1000 ml/min, preferably at least 2 ml/min, but no more than 500 ml/min, and more preferably with a flow rate of at least 3 mL/min and no more than 200 mL/min. The corresponding flux across each filter is at least 1 L/hr/m2 but no more than 2000 L/hr/m2, preferably 3 L/hr/m2 to 1500 L/hr/m2, and most preferably at least 125 L/hr/m2 but no more than 250 L/hr/m2. Filters are connected in series, usually with medical grade silicone tubing. Preferably, the initial filter (Filter #1) or the initial two filters (Filters #1 and #2) are matrix filters and are made of polypropylene, however, nylon, mixed cellulose ester and borosilicate glass or other material known to those in the art may be used. Preferably, the penultimate filter (Filter #3) is a membrane filter, most preferably a track-etched polycarbonate filter, although other filters with similar properties known to those in the art may be used. For aseptic procedures, the filters are sterile. In an embodiment, three filters (Filter #1, Filter #2 and Filter #3) are connected in series and sporozoites are captured by dead end filtration on Filter #4. Additional filters may be used. Alternatively, only one or two filters may be used (as discussed below in Paragraph 59), however using three filters is optimal. In an embodiment, filter #1 is a membrane matrix with a nominal pore size of at least about 2.5 microns, but no more than about 30 microns, preferably at least about 5 microns, but no more than 20 microns. In one embodiment the filter used has a nominal pore size of about 10 microns with a filtration area of 17.5 cm$^2$. (Polygard®-CN Optiscale—Millipore Cat. No. SN1HA47HH3). In a scaled up embodiment the filtration area is 1800 cm2. The nominal pore size of Filter #2 (also a membrane matrix) is at least about 0.3 microns but not larger than about 1.2 microns. In one embodiment, the pore size is about 0.6 micron with a filtration area of 17.5 cm2. (Polygard®-CN Optiscale filter—Millipore Cat. No. SN06A47HH3)—smaller than the diameter of *Plasmodium*. In a scaled up embodiment the filtration area is 1800 cm2. In one embodiment, Filter #3 is a track-etched membrane filter with precise pore diameter and consistent pore size, and has a pore size of at least 1.2 microns but not larger than 3 microns—larger than the nominal pore size of the preceding filter. In one embodiment the filter used has a pore size of 1.2 microns with a filtration area of 11.3 cm2. (Isopore membrane, 47 mm in diameter—Millipore Cat. No. RTTP04700) held in a Swin-Loc filter holder (Whatman Cat. No. 420400). In a scaled up embodiment the filtration area is 127 cm2. Filtered material is captured on Filter #4 in a stirred ultrafiltration cell (Millipore, model 8200) fitted with an Isopore membrane, 90 mm in diameter with a filtration area of 28.7 cm2, and a track-etched pore size of no more than 0.8 microns, preferably no more than 0.6 microns, and preferably no more than 0.2 microns. In one embodiment the pore size is 0.4 microns (Millipore Cat. No. HTTP09030). In a scaled up embodiment the filtration area is 162 cm2. In another scaled up embodiment the filtration area is 63 cm2. The system is washed several times with media. When the retentate volume reaches about 40 ml in the stirred cell, the stirred cell container outlet is opened and drained by gravity leaving about 5-10 ml of residual retentate although the retentate volume can be reduced by other methods such as applying pressure from compressed gas such as nitrogen or a mechanical device such as a piston, gravity is the preferred method. This residual retentate is collected and transferred, together with three washes using purification media to a total of about 35 ml, typically in a sterile 35 ml Oak Ridge or similar centrifuge tube (the size of the tube will vary depending on the volume of the preparation). Purified sporozoites in media in the 35 ml Oak Ridge tube are centrifuged at 5,000 g to 25,000 g, preferably at 16,300 g, for 2 minutes to 12 minutes, preferably five minutes, to pellet the sporozoites. The supernatant media is decanted. This step additionally purifies the sporozoite preparation by removing smaller more buoyant materials and soluble materials that remain in the supernatant.

Using the 3 size-exclusion filter methodology, this procedure provides greater than a substantial reduction of attendant material in the purified sporozoite preparation relative to the attendant material in the pre-purification preparation (reduction factor) of from 200 to 10,000 fold. The amount of residual SGM in purified preparations of sterile purified sporozoites routinely is less than 25 ng of attendant material per 25,000 sporozoites (greater than 97% reduction relative to the initial amount of SGM), preferably less than 15 ng per 25,000 (98% reduction) sporozoites, and more preferably less than 1 ng per 25,000 sporozoites (99.9%). The contaminating SGM in each purified preparation described herein is usually reduced several thousand fold relative to SGM in the initial triturated pre-purified salivary gland material from which each purified preparation is derived. Preferably the purification reduction factor is at least 15-fold, more preferably, the purification factor is at least 1,500-fold and most preferably at least 3,500-fold. The geometric mean of the reduction factor in the 10 campaigns described in Example 1 is 1625, a 99.93% reduction in SGM during the purification process.

For example, purified sporozoite preparations, isolated from dissected mosquito salivary glands shown in Example 1 (Table 2) contained a range of from 0.19 ng to 1.01 ng SGM per 25,000 sporozoites and the percentage reduction of attendant SGM ranged from 99.91% to 99.97%. Alternatively, the method described in Paragraph 59 below provided a preparation of sporozoites with no more than 85 ng SGM per 25,000 (95% reduction of attendant SGM material) and are considered substantially purified. The geometric mean of SGM in purified preparations from the 10 production campaigns in Table 2 (using 3 size exclusion filers) was 0.51 ng SGM per 25,000 sporozoites with a 95% confidence interval of from 0.34 to 0.67 ng SGM per 25,000 sporozoites.

In an alternative embodiment, Filter #3 is eliminated from the filter train described in Paragraph 56 above and a 2 size-exclusion filter methodology (Intermediate Filter #1 and Filter #2) is used. Sporozoites are captured as described in Paragraph 56 above. In an example of this embodiment, a crude preparation of 1,555 ng/25,000 sporozoites was loaded and purified as described (minus Filter #3). After collection (either on a 0.4 micron or 0.45 micron filter) and resuspension, the purified preparation contained 84 ng/25,000 sporozoites. Here, the reduction factor was greater than 18 fold and 94.6% of SGM contamination was removed. This preparation is considered substantially purified.

The range of the yield of purified sporozoites was between 30% and 100% of the number of sporozoites in the starting preparation—usually between 50% and 70%.

This method is effective at reducing contamination in a crude sporozoite preparation. The sporozoites are then preserved. In an embodiment, the sporozoites are cryopreserved (Leef J. L. et al. Bull WHO 57 (suppl 1) (1979) 87-91; Orjih A. U., F. and Nussenzweig R S. Am. J. TroP. Med. Hyg. (1980) 29(3): 343-7). In an embodiment, the sporozoites are preserved by lyophilization. In an embodiment, the sporozoites are preserved by refrigeration. Other methods of preservation are known to those skilled in the art.

Attenuation

Several means of inducing *Plasmodium* sporozoite attenuation are known. These include heritable genetic alteration, gene mutation, radiation exposure, and exposure to mutagenic chemicals, exposure to metabolic inhibition chemicals and exposure to environmental conditions such as high or low temperature or pressure.

Methods of inducing attenuation of sporozoites by radiation exposure have been disclosed (See, e.g., Hoffman & Luke, U.S. Pat. No. 7,229,627; US Pub. No. 2005/0220822) and are incorporated herein by reference. Sporozoites may be attenuated by at least 100 Gy but no more than 1000 Gy, preferably 120 to 200 Gy, and most preferably about 150 Gy. The attenuation of *Plasmodium* parasites of the vaccine disclosed herein allow sporozoite-stage parasites to remain metabolically active, infectious with the ability to invade hepatocytes (potency); while ensuring that parasites do not develop to the fully mature liver schizont stage, cannot reenter the host bloodstream, invade erythrocytes or reach the developmental stages which cause disease (safety). Those of skill in the art can routinely determine the developmental stages of the parasite and adjust the attenuation as necessary.

The biology of the *Plasmodium* infection of hepatocytes provides opportunities for in vitro assays to demonstrate both potency and safety. Normally, sporozoites migrate from the bite site of the mosquito to the liver, primarily via the blood stream, but potentially via the lymphatic system. In the liver they multiply within hepatocytes, producing, in the case of *P. falciparum*, about 10,000-40,000 progeny (merozoites) per infected cell. These liver stage parasites express multiple proteins, which are not expressed in sporozoites or at later developmental stages. After developing in the liver to the merozoite stage, they are released from hepatocytes and reenter the blood stream, expressing a different set of stage-specific proteins—different from those expressed during the sporozoite and early hepatic stages—and invade erythrocytes, where additional multiplication increases parasite numbers by approximately 10 to 20 fold every 48 hours. Unlike the five to ten day development in the liver, which does not induce any symptoms or signs of illness, untreated blood stage infection causes hemolysis, shaking chills, high fevers, and prostration, and many other symptoms and signs of malaria.

Potency Assay

The level of infectious potency of purified radiation-attenuated *P. falciparum* sporozoites may be assessed by measuring the expression of *P. falciparum* Liver Stage Antigen-1 (PfLSA-1) in human hepatocyte cultures using an immunofluorescence assay (IFA). PfLSA-1 is a protein that is not expressed by sporozoites, but is expressed by *P. falciparum* parasites (both attenuated and wild type) after they have successfully invaded hepatocytes (FIG. 3). Expression of PfLSA-1 indicates that the attenuated sporozoites are metabolically active.

Human hepatocytes (cell-line HC-04 [1F9], See Prachumsri, J. and N. Yimamnuaychok, U.S. Pat. No. 7,015,036) are seeded approximately 24±6 hours pre-infection using a 1:1 ratio of Dulbecco's modified Eagle's medium and F-12 Ham's mixture supplemented with 10% fetal bovine serum and 2% penicillin/streptomycin solution (HC-04 growth medium). The cells are seeded at a concentration of $4.0 \times 10^4$ cells/0.3 ml/well into 8-well Lab Tek Permanox (NUNC) chamber slides coated with Entactin Collagen-IV Laminin (ECL) (Upstate) and incubated at 37±1° C., 5% CO2 and 80% relative humidity. When the monolayer confluency reaches ≥80% at 24±6 hours post-seeding, the culture supernatant is aspirated from each well, replaced with 0.3 ml of fresh HC-04 growth medium and returned to the incubator.

Attenuated *P. falciparum* sporozoites are diluted with HC-04 growth medium to a concentration of 500 sporozoites/µl. Fifty µl of the diluted parasite sample is then added to each well, after aspirating 300 µl of medium, allowing a total of $2.5 \times 10^4$ cells to infect the HC-04 cells in each well. Infected hepatocytes are incubated for 3±0.5 hours, washed three times with HC-04 growth medium by gentle aspiration of the supernatant and cultured with 0.3 ml of fresh medium per well. Cultures are observed daily for three days for any indication of the presence of contamination. In the absence of contamination, the culture supernatant is aspirated from individual wells and replaced with 0.3 ml of fresh HC-04 growth medium daily and returned to the incubator. At 72±6 hours post infection, cultures are observed microscopically for possible contamination. In the absence of contamination, the cultures are washed three times using 0.3 ml of phosphate buffered saline (PBS), fixed at room temperature with 0.3 ml of cold methanol (stored at −20° C.), washed another three times using 0.3 ml of PBS and stored in 0.3 ml of the same. Slides can be stored in a refrigerator at 2-8° C. for up to 72 hours until they are stained for immunofluorescence using an anti-PfLSA-1 polyclonal rabbit serum as the primary antibody and an Alexa fluor-488 labeled anti-rabbit secondary antibody. The plastic chamber and gasket are removed from stained slides. Slides are mounted using Vectashield mounting medium (Vector) and covered with a cover sliP. Slides are evaluated by counting all parasites expressing PfLSA-1 per well using an epifluorescence microscope with phase contrast (FIG. 3). The sporozoites are considered potent if there is no contamination of the preparations at any step and the number of fluorescing parasites is at least 200/well.

Vaccine Compositions

Pharmaceutical compositions comprising live *Plasmodium* sporozoites, both attenuated and pathogenic, and methods of using these compositions as preventive vaccine compositions to prevent disease, and as pathogenic challenge compositions to infect volunteers in the testing of vaccines and drugs, have been provided (see particularly Hoffman USSN US2005/0220822). Various categories of attenuated sporozoites have been considered for use in vaccines. These include sporozoites attenuated by various methods including heritable genetic alteration, gene mutation, radiation exposure, and chemical exposure. Various attenuated isolates created by direct genetic manipulation of the parasites have been described for *P. falciparum* (van Schaijk et al. PLoS ONE (2008) 3:e3549) as well as murine-specific *Plasmodium* species (Kappe et al. U.S. Pat. No. 7,122,179; van Dijk et al. PNAS (2005) 102:12194-12199; Labaied et al. Infect Immun. (2007) 75:3758). In an embodiment, radiation attenuation of human-specific *Plasmodium* is achieved by exposure to gamma radiation. (Hoffman, S. L. et al. (2002) 185:1155-1164). The purification processes provided herein are intended for purification of fully infectious sporozoites as well as attenuated sporozoites.

In an embodiment, attenuated *Plasmodium* sporozoites may be genetically manipulated to contain exogenous genes of other *Plasmodium*-species or of other pathogenic organisms which may be expressed prior to, during or subsequent to infection.

Vaccination methodologies comprising purified pathogenic sporozoites are also contemplated. For instance, pathogenic sporozoites may be administered to individuals concurrently treated with anti-malarials (e.g. chloroquine) effective against the asexual erythrocyte stage parasites, or administered to individuals subsequently treated with anti-malarials effective against the asexual erythrocyte stage parasites, thereby preventing the pathology caused by the parasites in vivo, while allowing the parasites to stimulate protective immune responses. Roestenberg, M., et al. (2009) NEJM 361:468-478; Pombo, D. J. et al. (2002) Lancet 360:610-617.

Sterile, purified pathogenic sporozoites are also useful in challenge protocols to assess the effectiveness of vaccines and vaccination methodologies in challenge studies of volunteers previously treated with these vaccines and vaccine methodologies. Similarly, purified pathogenic sporozoites are useful to generate the symptoms, signs or pathology of malaria in studies to assess the effectiveness of chemoprophylactic drugs and therapeutics.

Sterile live pathogenic sporozoites that have been purified, as well as sterile live attenuated sporozoites that have been purified are generally more useful than their non-sterile, unpurified counterparts because compositions and vaccines comprising sterile purified sporozoites reduce or eliminate the risk that attendant material or contamination will cause unwanted immune responses, adventitious infections or other unexpected consequences. Vaccines comprising purified live attenuated *Plasmodium* species sporozoites usually are administered parenterally, and by other routes as described herein. Such vaccines are useful for prevention or reduction of severity of malaria, its manifestations, symptoms or its pathology.

In an embodiment, compositions and vaccines comprising aseptically prepared attenuated purified sporozoites provide partial, enhanced, or full protection in human and other mammalian subjects not previously exposed to a malaria-causing pathogen, or exposed, but not fully protected. These compositions and vaccines are similarly useful to reduce the chance of developing a disease-producing infection from parasites that causes malaria, including species of *Plasmodium*, e.g. *P. falciparum* or *P. vivax*, and the like, and reduce the chance of becoming ill when one is infected, reduce the severity of the illness, such as fever, when one becomes infected, reduce the concentration of parasites in the infected person, or reduce mortality rates from malaria in populations exposed to malaria parasites. In many cases even partial protection or delay in the time it takes an immunized individual as compared to a non-immunized individual to become infected with the parasites or ill from infection is beneficial. Similarly, a vaccine treatment strategy that results in any of these benefits in about 30% of a population may have a significant impact on the health of a community and of the individuals residing in the community. In other embodiments comprising pathogenic sporozoites, compositions disclosed are useful for demonstrating the efficacy of vaccines, drugs for the treatment of malaria, and other treatments and preventions of malaria.

Provided are methods for prevention of malaria in a subject. The methods comprise administering to the subject a vaccine which has been prepared aseptically and comprises substantially purified live attenuated *Plasmodium* sporozoites in an amount effective to prevent malaria.

The subject to which the vaccine is administered in accordance with these methods may be any human or other mammal, susceptible to infection with a malaria parasite. For such methods, administration can be via the alimentary tract, such as oral, or administration can be parenteral, including, but not limited to mucosal, intranasal, epidermal, cutaneous, intramuscular, subcutaneous, intradermal, submucosal, intravenous and the like. Moreover, the administration may be by continuous infusion or by single or multiple boluses as well as delivery mediated by microneedles.

The prevention and/or treatment of malaria may be readily ascertained by the skilled practitioner by evaluation of clinical or pathological manifestations associated with malarial infection, for example elevated temperature, headache, fatigue, coma, or percent of erythrocytes parasitized. Thus, according to the methods of the present invention, the subject shows improved or absent clinical signs, symptoms or pathological manifestations of malaria following administration of a vaccine comprising purified live attenuated *Plasmodium* sporozoites.

Effective and optimal dosage ranges for vaccines and immunogens can be determined using methods known in the art. Guidance as to appropriate dosages to achieve an anti-malarial effect is provided from the exemplified assays disclosed herein. More specifically, results from the immunization pattern described herein and in cited references can be extrapolated by persons having skill in the requisite art to provide a test vaccination schedule. Volunteer subjects are inoculated with varying dosages at scheduled intervals and test blood samples are evaluated for levels of protection against malaria upon subsequent challenge with infective parasites. Such results can be used to refine an optimized immunization dose and dosage regimen (schedule) for effective immunization of mammalian, specifically human, subjects. A dose effective in conferring a protective immunity is from 5,000 to 400,000 purified attenuated sporozoites administered in a dosage regimen of 1 to 6 doses, more particularly a dose of from 15,000 to 270,000 purified attenuated sporozoites in a dosage regimen of at least 2 doses, and most particularly a dose of from 25,000 to 150,000 purified attenuated sporozoites in a dosage regimen of 3 or 4 doses.

An immune response in a subject can be measured by standard tests including, but not limited to the assessment of humoral and cellular immune responses, including, but not limited to: measurement of antigen specific or parasite stage specific antibody responses; direct measurement of peripheral blood lymphocytes by means known to the art; natural killer cell cytotoxicity assays (Provinciali et al. (1992) J. Immunol. Meth. 155: 19-24), cell proliferation assays (Vollenweider et al. (1992) J. Immunol. Meth. 149: 133-135), immunoassays of immune cells and subsets (Loeffler et al. (1992) Cytom. 13: 169-174; Rivoltini et al. (1992) Can. Immunol. Immunother. 34: 241-251); and skin tests for cell mediated immunity (Chang et al. (1993) Cancer Res. 53: 1043-1050). Various methods and analyses for measuring the strength of the immune system have been described, for example, Coligan et al. (Ed.) (2000) Current Protocols in Immunology, Vol. 1, Wiley & Sons.

The vaccines provided comprise aseptic and non-aseptic compositions of purified live attenuated *Plasmodium* sporozoite substantially free of attendant material, and compositions with a pharmaceutically acceptable diluent, excipient, or carrier. These vaccines are effective in preventing or mitigating malaria upon subsequent challenge with infectious parasites. Methods of formulating pharmaceutical compositions and vaccines are well known to those of ordinary skill in the art (see, e.g., Remington, The Science and Practice of Pharmacy 21st Edition, Hendrickson, ed. (USIP: 2005)).

Comprehended by the invention are vaccine compositions, aseptically prepared or otherwise, comprising purified, live attenuated or non-attenuated *Plasmodium* sporozoites along with appropriate diluent and buffer. Diluents, commonly Phosphate Buffered Saline (PBS), or Normal Saline (NS), are of various buffer content pH and ionic strength. Such compositions may also include an excipient such as serum albumin, particularly human serum albumin. Serum albumin may be purified from naturally occurring sources such as human blood, or be produced by recombinant DNA or synthesis technologies. Such compositions may also include additives such as anti-oxidants e.g., ascorbic acid, sodium metabisulfite, and/or preservatives or cryopreservatives. Incorporation of the material into particulate preparations of polymeric compounds such as polylactic acid, polyglycolic acid, etc. or into liposomes may also be used. (See, e.g., Remington's Pharmaceutical Sciences, 18th Ed. (1990), Mack Publishing Co., Easton, Pa. 18042) pages 1435-1712 which are herein incorporated by reference.

In order to determine the effective amount of the vaccines, the ordinary skilled practitioner, considering the therapeutic context, age, and general health of the recipient, will be able to ascertain proper dosing. The selected dosage depends upon the desired therapeutic effect, on the route of administration, and on the duration of the treatment desired. Experiments to determine levels for dosages can be ascertained by one of ordinary skill in the art by appropriate human clinical trials in which various dosage regimens are evaluated for their capacity to elicit protection against malaria.

Disclosed vaccines and disclosed methods of using these vaccines may be useful as one component in a vaccine regimen, each component in turn comprising a discrete vaccine to be administered separately to a subject. Regimens may include sequential immunization with attenuated *Plasmodium* species sporozoites and other types of *Plasmodium* vaccines, so-called, prime-boost strategies. This may include attenuated sporozoites as a prime, and *Plasmodium*-related recombinant protein or proteins in adjuvant as a boost or vice versa. This may also include *Plasmodium*-related DNA vaccines or a recombinant virus, such as adenovirus, that express *Plasmodium*-related proteins, as a prime and purified, attenuated sporozoites vaccine as a boost, or vice versa. It may also include sequential or mixed immunization with attenuated *Plasmodium* species sporozoites and some form of erythrocytic stage parasites, including, killed and live attenuated. A vaccine complex comprising separate components may be referred to as a vaccine regimen, a prime/boost regimen, component vaccine, a component vaccine kit or a component vaccine package, comprising separate vaccine components. For example, a vaccine complex may comprise as a component, a vaccine comprising purified, aseptic, live attenuated sporozoites. The complex may additionally comprise one or more recombinant or synthetic subunit vaccine components, including but not limited to recombinant protein, synthetic polypeptide, DNA encoding these elements per se or functionally incorporated in recombinant virus, recombinant bacteria, or recombinant parasite. A vaccine component may also include aseptic attenuated axenic sporozoites that are allowed to develop to the early liver stage extracellularly.

*P. falciparum* strains from different parts of the world—West Africa, East Africa, SE Asia, and the like, have been described. Volunteers immunized with one strain of attenuated sporozoite exhibit protection against others strains (Hoffman, S. L. et al (2002) J. Inf. Dis. 185:1155-1164). In an embodiment, multiple isolates and/or strains of a *Plasmodium* species are combined in a sporozoite composition or in a vaccine formulation.

Several *Plasmodium* species are known to cause malaria in humans, predominantly *P. falciparum* and *P. vivax*. Other *Plasmodium* species cause malaria as well, including *P. malariae*, and *P. ovale*. *P. knowlesi* is also known to cause human disease. In an embodiment, two or more *Plasmodium* species are combined in a vaccine formulation. In still other embodiments, separate components of a vaccine regimen may be derived from different species, e.g., some doses from *P. falciparum* and others from *P. vivax*.

In another embodiment, the sporozoite may be a transgenic or recombinant parasite, i.e. a parasite that includes and expresses a DNA sequence or gene that is foreign to the species of parasite which contains it, referred to herein as a transgene. (See, e.g. Franke-Fayard, et al. Molec. and Biochem. Parasitol. 2004 A *Plasmodium berghei* reference line that constitutively expresses GFP at a high level throughout the complete life cycle. 137:23-33; Wengelnik, K. et al. The EMBO J. 1999 The A-domain and the thrombospondin-related motif of *Plasmodium falciparum* TRAP are implicated in the invasion process of mosquito salivary glands. 18:5195-5204). It will be understood by those skilled in the art that a transgenic parasite, i.e. containing a transgene, can be purified according to the methodology disclosed herein in the same fashion and to the same degree as the parental parasite from which the transgenic parasite was created.

Recently published results report cross-species protection in a rodent malaria system that has been shown to have a high degree of predictability for what occurs with the human malaria system (Sedegah, M. et al (2007) Parasite Immunol. 29:559-565). This suggests that a vaccine composition comprising *P. falciparum* may provide protective immunity against *P. vivax* and/or other human *Plasmodium* species.

Pharmaceutical compositions may be preserved, cryopreserved, lyophilized, spray-dried, refrigerated, or thermostabilized at room temperature and the like.

Both the foregoing description and the following examples are exemplary and explanatory only and are not restrictive of the invention, as claimed. Moreover, the invention is not limited to the particular embodiments described, as such may, of course, vary. Further, the terminology used to describe particular embodiments is not intended to be limiting, since the scope of the present invention will be limited only by its claims.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all patents, patent applications and publications mentioned herein are incorporated herein by reference.

As used herein and in the appended claims, the singular forms "a," "or," and "the" include plural referents unless the context clearly dictates otherwise. Thus, for example, reference to "an attenuated sporozoite vaccine" includes a plurality of such sporozoites and reference to "the agent" includes reference to one or more agents and equivalents thereof known to those skilled in the art, and so forth.

Furthermore, sporozoites which are metabolically active, and alive but attenuated in their life cycle and ability to cause the clinical manifestations and pathology of malaria are variously referred to as attenuated, live attenuated and metabolically active, live attenuated.

The numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value arrived at from an experimental measurement, however, inherently contains certain errors from the standard deviation of its experimental measurement.

Many modifications and variations of the present invention are possible in light of the above teachings. It is therefore to be understood that, within the scope of the appended claims, the invention many be practiced otherwise than as specifically described.

The following examples further illustrate the invention. They are merely illustrative of the invention and disclose various beneficial properties of certain embodiments of the invention. These examples should not be construed as limiting the invention.

EXAMPLES

Example 1

Attendant SGM Determination—ELISA

Sporozoites of any *Plasmodium* species may be purified by the methods provided. The examples provided herein describe the purification of the sporozoites of *P. falciparum* (PfSPZ). However, other embodiments utilize *P. vivax, P. ovale, P. malariae,* and/or *P. knowlesi*. Still other embodiments utilize mixtures of these parasites. Still other embodiments utilize attenuated sporozoites of each species. Still other embodiments utilize attenuated sporozoites that include and express a DNA sequence or gene that is foreign to that parasite.

A—Preparation of Anti-SGM Rabbit Anti-SERA i) Extraction of Salivary Glands from Mosquitoes To generate rabbit anti-sera against mosquito salivary glands, 10 to 14 day old insectary-raised *Anopheles stephensi* mosquitoes were immobilized by placing in a 4° C. refrigerator for approximately five minutes. Immobilized mosquitoes were placed briefly in a Petri dish containing 70% ethanol and then transferred into a Petri dish containing 1× phosphate buffered saline (PBS). A pair of salivary glands from each mosquito was dissected by hand in 1×PBS on a microscope glass slide and transferred to a 1.7 ml clear sterile microtube (Axygen Scientific Inc. CA) containing 20-30 µl of 1×PBS. On a daily basis, approximately 100 mosquitoes were dissected and 100 pairs of salivary glands in 30 µl PBS were placed in a freezer at −70° C. When enough salivary glands had been obtained for one immunization, vials were removed from the freezer, thawed to room temperature and pooled.

ii) Salivary Gland Processing

For the primary inoculation, salivary glands were dissected from 1,000 mosquitoes and stored at −70° C. On the day of inoculation, samples were thawed, pooled and lysed by three additional freeze-thaw cycles using a dry ice/ethanol bath and thawing at room temperature. The salivary glands were reconstituted in a final volume of 600 µl of 1×PBS and emulsified with Montanide ISA 720 (SEPPIC, Inc., Fairfield, N.J.).

For all subsequent immunizations, salivary glands were dissected from 500 mosquitoes and stored at −70° C. daily. On the day of inoculation, samples were thawed, pooled and homogenized with a pestle (Kontes EF2488A). The pestle was rinsed with 100 µl of PBS which was added to the pool. The sample was reconstituted to a final volume of 600 µl PBS and emulsified within 30 minutes after reconstitution.

iii) Salivary Gland Emulsification

Two ml glass vials (two vials for adjuvant control; two vials for salivary glands in adjuvant) were obtained. Seven hundred fifty µl of Montanide ISA 720 adjuvant was drawn through a 5 micron filter syringe. Seven hundred µl of the filtered adjuvant was injected into each glass vial. Three hundred µl of PBS was added to the control vial and three hundred µl of salivary glands in PBS to the experimental vial. The vials were covered with a rubber stopper. Each vial was further capped with an aluminum seal cap and the seal was pressed with a crimper. Vials were placed in the small holes of a vortex pad, taped down, and vortexed for 30 minutes.

iv) Emulsion and Inoculation Quantities

For the primary immunization two glass vials were used to emulsify antigen from 1,000 mosquitoes, (each containing 1,000 µl of a 300:700 volume ratio of salivary gland/PBS: Montanide adjuvant) yielding a total emulsion volume of 2 ml. For subsequent immunizations antigen from 500 mosquitoes was similarly emulsified in a total volume of 2,000 µl. Therefore half the concentration of antigen was injected in subsequent immunizations in the same emulsion volume as the primary inoculum. Control rabbits in all immunizations received 2 ml of emulsion containing a 300:700 volume ratio of PBS:adjuvant. All emulsions were inoculated into rabbits within one hour of emulsification.

Experimental rabbits received 2,000 µl of salivary glands: adjuvant (300:700 ratio by volume) emulsion injected subcutaneously at eight sites, 250 µl per site. Control rabbits received 2,000 µl of PBS:adjuvant (300:700 ratio by volume) emulsion injected subcutaneously at eight sites, 250 µl per site.

v) Rabbit Immunization Schedule

Table 1 provides the immunization schedule used to generate the polyclonal antibody used in the examples provided herein. This schedule is not intended to be limiting with regard to the method of polyclonal antibody preparation, but rather is provided only as an example and disclosure of antibody used herein

TABLE 1

| IMMUNIZATION SCHEDULE | |
|---|---|
| Time (days) | Procedure |
| 0 | Pre-bled two rabbits (one control and one experimental) for serum to be used as a reference to evaluate antibody titers. |
| 0 | First inoculation of experimental rabbit with 2,000 µl emulsion of salivary gland material dissected from 1,000 mosquitoes and control rabbit with 2,000 µl emulsion of 1X PBS and Montanide ISA 720. |
| 21 | Second inoculation of experimental rabbit with 2,000 µl emulsion of salivary gland material dissected from 500 mosquitoes and control rabbit with 2,000 µl emulsion of 1X PBS and Montanide ISA 720. |
| 30 | Test bled #1; pre-bleed and test sera received for evaluation |

TABLE 1-continued

IMMUNIZATION SCHEDULE

| Time (days) | Procedure |
|---|---|
| 42 | Third inoculation of experimental rabbit with 2,000 µl emulsion of salivary gland material dissected from 500 mosquitoes and control rabbit with 2,000 µl emulsion of 1X PBS and Montanide ISA 720 |
| 51 | Test bled #2; sera received for evaluation |
| 57 | Fourth inoculation of experimental rabbit with 2,000 µl emulsion of salivary gland material dissected from 500 mosquitoes and control rabbit with 2,000 µl emulsion of 1X PBS and Montanide ISA 720. |
| 66 | Test bled # 3; sera received for evaluation. |
| 92 | Based on results of test bleed #3 an additional inoculation of salivary gland material was administered. Fifth inoculation of experimental rabbit with 2,000 µl emulsion of salivary gland material dissected from 500 mosquitoes and control rabbit with 2,000 µl emulsion of 1x PBS and Montanide ISA 720. |
| 102 | Rabbits were exsanguinated and 45 ml serum was obtained from each rabbit. |

B—SGM ELISA Assay

An enzyme-linked immunosorbent assay (ELISA) was used to quantify attendant material. As an example, salivary gland material (SGM) originating from *A. stephensi* salivary glands in preparations of *P. falciparum* sporozoites was quantified. ELISA plates (Nunc MaxiSorp Cert, N/Ster, PS, 96 well Flat-Bottom Immuno Plate, Cat. No. 439454) with dilutions of SGM standards (prepared from salivary glands of uninfected mosquitoes) and samples of sporozoites from crude salivary gland preparations as well as samples of the purified sporozoite preparations were prepared for assay. The primary antibody was rabbit anti-SGM serum (described in A, above) diluted 1:200. Secondary antibody was alkaline phosphatase-conjugated anti-Rabbit IgG diluted 1:5,000 (Promega, Cat. No. S373B). KPL Blue Phos Substrate and Stop Kits (KPL, Cat No. 50-88-06 and 50-89-00) were used. Plates were read on a Molecular Devices Microplate Reader at 635 nm.

There are two components to the assay used to quantify SGM in the sporozoite preparations. The first consists of generating a standard curve with reference SGM of known concentration, and the second consists of quantifying the amount of SGM present in the pre-purification and post-purification samples. A fresh standard curve is generated for each assay using an SGM reference standard (RS-SGM) of known SGM concentration as capture antigen. To establish the standard curve, a serial dilution of decreasing concentration (2.0 to 0.05 µg/mL) of the RS-SGM was prepared in E-199 with 1% HSA. To assess residual SGM in pre-purification and post-purification sporozoite preparations, these samples were also serially diluted in E-199 with 1% HSA. Diluted RS-SGM samples and sporozoite preparations were further diluted to 0.25% HSA with 1xPBS and added to the ELISA plate in triplicate. This dilution into PBS is necessary because it lowers the content of HSA. HSA acts as a blocking agent and can decrease the sensitivity of the assay. The SGM-coated ELISA plates were incubated first with the rabbit polyclonal anti-SGM antiserum (see paragraph 100) and then with the enzyme-labeled anti-rabbit antibodies, and finally with an enzyme substrate (see paragraph 101). In the presence of SGM, the enzyme substrate changes color and the optical densities (ODs) of the contents of the wells change. The OD of each sample was determined using the microplate reader. To determine the amount of SGM in the sporozoite preparations, the OD values of these samples and the reference standard were fit with a logistic mixed model that has common asymptotes and slope but separate ED50 values for each sample. The relative values of the ED50 were used in combination with the known (or assigned) concentration of SGM in the reference sample to estimate the SGM concentration in the pre-purification sporozoite and VBP samples. The lower and upper 95% confidence limits were similarly determined for the sporozoite preparations from the overall data incorporating an estimate of variation based on three experimental assays that contained a common reference standard and test samples. From the numbers of sporozoites known to be present in each sporozoite preparation, the ng of SGM/25,000 sporozoites was calculated as were the reduction factors and percent reductions of the attendant material.

Table 2 shows the results of 10 production campaigns. "Start" represents measured amounts in ng SGM/25,000 sporozoites in crude preparations pooled after trituration of salivary glands dissected from infected mosquitoes. "Final" represents the corresponding measured amount of SGM in preparations which were purified by the methods provided herein. This methodology results in substantial purification of the sporozoites—99.9% or more.

It is recognized that the values arising from experimental measurements provided for ng SGM/25,000 sporozoites are based on results from the current assay as described, are not absolute, and may be somewhat different if another assay or method of analysis is used.

TABLE 2

PURIFICATION OF SPOROZOITES

| Campaign Number | ng[SGM]/ 25,000 spz | | Lower 95% CI | Upper 95% CI | Reduction Factor | Residual SGM (%) | % Reduction |
|---|---|---|---|---|---|---|---|
| | Start | Final | | | | | |
| 1 | 1,091.65 | 1.01 | 0.74 | 1.38 | 1,081 | 0.09 | 99.91 |
| 2 | 511.00 | 0.19 | 0.12 | 0.28 | 2,689 | 0.04 | 99.96 |
| 3 | 836.64 | 0.23 | 0.16 | 0.35 | 3,637 | 0.03 | 99.97 |
| 4 | 757.11 | 0.29 | 0.20 | 0.41 | 2,610 | 0.04 | 99.96 |
| 5 | 847.90 | 0.70 | 0.51 | 0.96 | 1,211 | 0.08 | 99.92 |

TABLE 2-continued

PURIFICATION OF SPOROZOITES

| Campaign Number | ng[SGM]/ 25,000 spz | | Lower 95% CI | Upper 95% CI | Reduction Factor | Residual SGM (%) | % Reduction |
|---|---|---|---|---|---|---|---|
| | Start | Final | | | | | |
| 6 | 780.66 | 0.65 | 0.47 | 0.90 | 1,201 | 0.08 | 99.92 |
| 7 | 893.88 | 0.61 | 0.44 | 0.85 | 1,465 | 0.07 | 99.93 |
| 8 | 407.37 | 0.29 | 0.19 | 0.44 | 1,404 | 0.07 | 99.93 |
| 9 | 508.42 | 0.35 | 0.24 | 0.52 | 1,452 | 0.07 | 99.93 |
| 10 | 719.45 | 0.67 | 0.48 | 0.94 | 1,073 | 0.09 | 99.91 |
| Geometric Mean[a] | 706.88 | 0.51 | 0.34 | 0.67 | 1,625 | 0.07 | 99.93 |

[a]Data comprising columns labeled 'Start', 'Reduction Factor' and 'Percent Reduction' are skewed. Therefore geometric means were calculated for these data. Data in the other columns were treated the same way for consistency.

Example 2

Purification of Sporozoites in Campaign 3

Sporozoites were purified from triturated salivary gland preparations using size exclusion filtration as disclosed. The sporozoites were maintained throughout the purification process in purification medium. At the end of the purification, samples were removed for visual observation (microscopic examination, bioburden testing (USP <61>), testing for *Mycoplasma* and *Spiroplasma*, in vitro determination of viral contaminants; and SGM-ELISA assay.

A—Purification of Sporozoites

Preparation of material for purification: The triturated dissection product from between 272 and 356 mosquitoes was received altogether in a tube. A sample (5 µl) of the dissection product was removed and set aside at 22° C. for visual observation after pooling (FIG. 1a). The remaining dissection product was then diluted to 10 ml with the purification media. A sample (total of 100 µl) was removed at this point for counting (20 µl) and the SGM assay (60 µl). All solutions and samples were kept at about 22° C. for the duration of the purification.

Purification procedure: Using a peristaltic pump at a flow rate of about 4 ml/min (about 140 L/hr/m2) the diluted dissection product was pumped across three filters (Filter #1, Filter #2 and Filter #3) connected in series and captured by dead end filtration on Filter #4. Filter #1, a depth filter, had a pore size of 10 microns (Polygard®-CN Optiscale—Millipore Cat. No. SN1HA47HH3). The pore size of Filter #2, a depth filter, was 0.6 micron (Polygard®-CN Optiscale filter—Millipore Cat. No. SN06A47HH3). Filter #3 had a pore size of 1.2 microns (Isopore membrane, 47 mm in diameter—Millipore Cat. No. RTTP04700) held in a Swin-Loc filter holder (Whatman Cat. No. 420400). Filtered material was captured on Filter #4 in a stirred ultrafiltration cell (Millipore, model 8200) fitted with a Isopore membrane, 90 mm in diameter and a pore size of 0.4 µm (Millipore Cat. No. HTTP09030). A total of 100 ml purification media for run #1 and a total of 120 ml for runs #2-5 were pumped across the membranes together with the diluted dissection product. This was followed with another 100 ml of purification media applied to Filter #4. When the retentate volume reached about 5-10 ml, it was collected together with washes using purification media in a total of 35 ml that was transferred to a sterile 35 ml Oak Ridge centrifuge tube. Another 35 ml wash was collected in a similar fashion and also transferred to a second sterile 35 ml Oak Ridge centrifuge tube. The 35 ml Oak Ridge tubes were centrifuged at 16,340 g for five minutes, and resuspended for counting, and held at about 22° C.

After counting, the material was resuspended to a concentration of about 15-18×10$^6$ sporozoites/ml. 150 µl was removed for assessment of SGM and stored frozen at −70° C. prior to performing the SGM-ELISA assay. 20 µl were removed from the purified PfSPZ preparation and applied to a microscope slide (FIG. 1b). Settling of sporozoites was allowed for at least 5 minutes, up to 30 minutes, and the sporozoites were viewed at 200× magnification. A similar procedure was carried out for the pre-purification sample (FIGS. 1a and 1b). The specific data for each run in the campaign are presented in Table 3 and a microscopic analysis (photomicrograph) of pre- and post-purification samples is presented in FIGS. 1a and 1b.

In campaign 3, seven runs using between 272 and 356 mosquitoes per run (2146 mosquitoes total) with yields of purified sporozoites per run ranging from 40% to 75% (mean 57%) giving a total of 61.3×10$^6$ purified sporozoites prior to removal of all samples for in-process and release assays. The SGM assay (Example 1—Table 2—Campaign 3) showed that the purified sporozoites contained 0.23 ng SGM/25,000 sporozoites. The SGM content of pooled pre-purification material contained 836.64 ng/25,000 sporozoites. In this example there was an overall 3,637 fold purification of sporozoites in the purification process. The modified USP <61> bioburden assay showed that there were no colony forming units, in other words no microbial contamination.

TABLE 3

Sporozoite Yield Campaign - 3

| | Start of Purification | | | End of Purification | |
|---|---|---|---|---|---|
| Run# | Mosquitoes dissected | PfSPZ/ Mosquito (×10$^{-3}$) | Total PfSPZ (×10$^{-6}$) | Total PfSPZ (×10$^{-6}$) | Yield (%)* |
| 1 | 356 | 36.5 | 13.0 | 9.8 | 75.4 |
| 2 | 330 | 43.9 | 14.5 | 9.2 | 63.4 |
| 3 | 272 | 57.9 | 15.8 | 6.6 | 41.8 |
| 4 | 298 | 47.8 | 14.3 | 10.6 | 74.1 |
| 5 | 326 | 65.2 | 21.3 | 12.7 | 59.6 |
| 6 | 274 | 65.2 | 17.9 | 8.1 | 45.3 |
| 7 | 290 | 37.1 | 10.8 | 4.3 | 39.8 |
| TOTAL | 2146 | | 107.6 | 61.3 | |
| MEAN | | 50.5 | | | 57.1 |

*% yield = 100 × (#SPZ at end/#SPZ at start)

Example 3

Purification of Sporozoites in Campaign 6

Sporozoites were purified from triturated salivary gland preparations using size exclusion filtration as described in Example 2 above. The sporozoites were maintained throughout the purification process in purification medium. Samples were removed for visual observation (microscopic examination), microbiological testing, and SGM-ELISA assay to quantify the amount of SGM in the samples. Samples were prepared and purified as in Example 2.

In campaign 6, eight runs using between 343 and 395 mosquitoes per run (2997 mosquitoes total) with yields of purified sporozoites per run ranging from 51% to 87.5% (mean 72.3%) giving a total of $160.5 \times 10^6$ purified sporozoites prior to removal of all samples for in-process and release assays (Table 4). The SGM-ELISA assay (Example 1—Table 2—Campaign 6) showed that the purified sporozoites contained 0.65 ng SGM/25,000 sporozoites. The SGM content of pooled pre-purification material contained 780.66 ng/25,000 sporozoites. In this example there was an overall 1,201-fold purification of sporozoites in the purification process. The modified USP <61> bioburden assay showed that there were no colony forming units, in other words no microbial contamination. Microscopic analyses (photomicrograph) of pre- and post-purification samples are presented in FIG. 2.

TABLE 4

Sporozoite Yield Campaign 6

| | Start of Purification | | | End of Purification | |
|---|---|---|---|---|---|
| Run# | Mosquitoes dissected | PfSPZ/ Mosquito $(\times 10^{-3})$ | Total PfSPZ $(\times 10^{-6})$ | Total PfSPZ $(\times 10^{-6})$ | Yield (%)* |
| 1 | 372 | 89.7 | 33.4 | 29.2 | 87.4 |
| 2 | 395 | 115.2 | 45.5 | 23.2 | 51.0 |
| 3 | 395 | 101.3 | 40.0 | 22.2 | 55.5 |
| 4 | 384 | 99.9 | 38.4 | 20.6 | 53.6 |
| 5 | 366 | 72.4 | 26.5 | 14.8 | 55.8 |
| 6 | 343 | 43.4 | 14.9 | 10.1 | 67.8 |
| 7 | 363 | 86.8 | 31.5 | 19.3 | 61.3 |
| 8 | 379 | 67.3 | 25.5 | 21.1 | 82.7 |
| TOTAL | 2997 | | 255.7 | 160.5 | |
| MEAN | | 84.5 | | | 64.4 |

*% yield = 100 × (#SPZ at end/#SPZ at start)

Example 4

Infection of a Human Hepatocyte Cell Line (HC-04 [1F9]) with Irradiated (150 Gy) P. falciparum Sporozoites from Campaigns 5, 6 and 7

Methods. PfSPZ were incubated for three days with HC-04 (1F9) cells, and then assessed for expression of PfLSA-1.

TABLE 5

PfLSA-1 expression in liver stage parasites after irradiation of PfSPZ.

| Campaign | PfSPZ/ well | Primary Antibody Against | Days in Culture | Number of Parasites Expressing PfLSA-1 | | | Mean/ well | STDEV |
|---|---|---|---|---|---|---|---|---|
| | | | | Well 1 | Well 2 | Well 3 | | |
| 5 | 25,000 | PfLSA-1 | 3 | 356 | 327 | 387 | 356.7 | 30.01 |
| 6 | 25,000 | PfLSA-1 | 3 | 401 | 359 | 378 | 379.3 | 21.03 |
| 7 | 25,000 | PfLSA-1 | 3 | 426 | 369 | 381 | 392.0 | 30.05 |

Results and Interpretation. Detection of *Plasmodium falciparum* liver stage antigen-1 (PfLSA-1), expressed in liver stage parasites, is an indication of the potency of attenuated and purified sporozoites. As shown in Table 5, PfLSA-1 is expressed by *P. falciparum* liver stage parasites after the sporozoites have been exposed to 150 Gy.

Example 5

Infection of a Human Hepatocyte Cell Line (HC-04 [1F9]) with Irradiated (100, 120, 142.5, 150 Gy) or Non-Irradiated *P. falciparum* Sporozoites Methods. Sporozoites were incubated for three days in HC-04 (1F9) cells, and then assessed for expression of PfLSA-1.

TABLE 6

Number of liver stage parasites expressing PfLSA-1 after different irradiation doses.

| Radiation Dose (Gy) | Number of Parasites Expressing PfLSA-1 per Well | | | | STD DEV | % CV |
|---|---|---|---|---|---|---|
| | Well 1 | Well 2 | Well 3 | Mean | | |
| 0 | 363 | 322 | 341 | 342.0 | 20.52 | 1.37 |
| 100 | 321 | 302 | 287 | 303.3 | 17.04 | 1.21 |
| 120 | 286 | 307 | 323 | 305.3 | 18.56 | 1.22 |
| 142.5 | 318 | 337 | 293 | 316.0 | 22.07 | 1.26 |
| 150 | 341 | 309 | 285 | 311.7 | 28.10 | 1.25 |

Results and Interpretation. 25,000 PfSPZ, which had been exposed to different radiation doses as indicated (Table 6), were added to each well of 8-well Lab-Tek slides containing HC-04 (1F9) cells. The slides were incubated for 3 days and assessed for parasites expressing PfLSA-1. As shown in Table 6, compared to non-irradiated Pf sporozoites, Pf sporozoites that were exposed to 150 Gy had 91% of the activity of non-irradiated Pf sporozoites in this assay. This difference did not reach the level of statistical significance in a two-tailed Student's t-Test (p=0.21).

Other embodiments of the invention will be apparent to those skilled in the art from consideration of the specification and practice of the invention disclosed herein. It is intended that the specification and examples be considered as exemplary only. Furthermore, in the foregoing, the present invention has been described with reference to suitable embodiments, but these embodiments are only for purposes of understanding the invention. Various alterations or modifications are possible so long as the present invention does not deviate from the claims, which provide a true scope and spirit of the invention.

What is claimed is:

1. A method of assessing the effectiveness of an antimalarial vaccine in a human subject previously treated with said antimalarial vaccine, said method comprising:
   challenging said subject with one or more doses of a composition comprising purified, pathogenic *Plasmodium*-species parasites, wherein said composition comprises less than 85 ng of attendant material per 25,000 sporozoites; and
   evaluating said subject for signs, symptoms, or pathology of malaria.

2. The method of claim 1, wherein said composition is prepared aseptically.

3. The method of claim 1, wherein the species of *Plasmodium* is *P. falciparum, P. vivax, P. ovale, P. knowlesi,* or *P. malariae.*

4. The method of claim 3, wherein the species of *Plasmodium* is *P. falciparum.*

5. The method of claim 1, wherein said composition comprises less than 15 ng of attendant material per 25,000 sporozoites.

6. The method of claim 5, wherein said composition comprises less than 1 ng of attendant material per 25,000 sporozoites.

7. The method of claim 6, wherein said composition comprises less than 0.12 ng of attendant material per 25,000 sporozoites.

8. A method of assessing the effectiveness of an antimalarial drug in a human subject, said method comprising:
   challenging said subject with one or more doses of a composition comprising purified, pathogenic *Plasmodium*-species parasites, wherein said composition comprises less than 85 ng of attendant material per 25,000 sporozoites;
   administering said antimalarial drug to said subject; and
   evaluating said subject for signs, symptoms, or pathology of malaria.

9. The method of claim 8, wherein said composition is prepared aseptically.

10. The method of claim 8, wherein the species of *Plasmodium* is *P. falciparum, P. vivax, P. ovale, P. knowlesi,* or *P. malariae.*

11. The method of claim 10, wherein the species of *Plasmodium* is *P. falciparum.*

12. The method of claim 8, wherein said composition comprises less than 15 ng of attendant material per 25,000 sporozoites.

13. The method of claim 12, wherein said composition comprises less than 1 ng of attendant material per 25,000 sporozoites.

14. The method of claim 13, wherein said composition comprises less than 0.12 ng of attendant material per 25,000 sporozoites.

* * * * *

UNITED STATES PATENT AND TRADEMARK OFFICE
CERTIFICATE OF CORRECTION

PATENT NO. : 9,616,115 B2
APPLICATION NO. : 15/002443
DATED : April 11, 2017
INVENTOR(S) : Sim et al.

It is certified that error appears in the above-identified patent and that said Letters Patent is hereby corrected as shown below:

In the Specification

At Column 1, immediately before the "BACKGROUND OF THE INVENTION," please insert the following paragraph:
--STATEMENT OF GOVERNMENT SUPPORT
The invention was made with government support under Grant Nos. 1R43AI058375 and 2R44AI05529 awarded by the National Institute of Health (NIH) and under Contract No. 05-01-0355 awarded by the Department of Defense/Congressionally Directed Medical Research Programs (CDMRP). The government has certain rights in the invention.--

Signed and Sealed this
Seventeenth Day of September, 2019

Andrei Iancu
*Director of the United States Patent and Trademark Office*

UNITED STATES PATENT AND TRADEMARK OFFICE
CERTIFICATE OF CORRECTION

PATENT NO. : 9,616,115 B2
APPLICATION NO. : 15/002443
DATED : April 11, 2017
INVENTOR(S) : Sim et al.

It is certified that error appears in the above-identified patent and that said Letters Patent is hereby corrected as shown below:

In the Specification

At Column 1, Line 22, immediately before the "BACKGROUND OF THE INVENTION," please replace the following paragraph:
"STATEMENT OF GOVERNMENT SUPPORT
The invention was made with government support under Grant Nos. 1R43AI058375 and 2R44AI05529 awarded by the National Institute of Health (NIH) and under Contract No. 05-01-0355 awarded by the Department of Defense/Congressionally Directed Medical Research Programs (CDMRP). The government has certain rights in the invention."
With:
--STATEMENT OF GOVERNMENT SUPPORT
The invention was made with government support under Grant Nos. 1R43AI058375 and 2R44AI055229 awarded by the National Institute of Health (NIH) and under Contract No. 05-01-0355 awarded by the Department of Defense/Congressionally Directed Medical Research Programs (CDMRP). The government has certain rights in the invention.--

This certificate supersedes the Certificate of Correction issued September 17, 2019.

Signed and Sealed this
Thirtieth Day of January, 2024

Katherine Kelly Vidal
*Director of the United States Patent and Trademark Office*